United States Patent [19]

LaVallie et al.

[11] Patent Number: 5,846,770
[45] Date of Patent: Dec. 8, 1998

[54] DNA MOLECULES ENCODING HUMAN CHORDIN

[75] Inventors: Edward R. LaVallie, Tewksbury; Lisa A. Racie, Acton, both of Mass.; Edward M. DeRobertis, Pacific Palisades, Calif.

[73] Assignee: Genetics Institute, Inc., Cambridge, Mass.

[21] Appl. No.: 749,169

[22] Filed: Nov. 14, 1996

Related U.S. Application Data

[63] Continuation-in-part of Ser. No. 343,760, Nov. 22, 1994, Pat. No. 5,679,783.

[51] Int. Cl.$^6$ .......................... C12P 21/00; C12N 15/00; C12N 1/21; C07H 21/04

[52] U.S. Cl. .................. 435/69.1; 435/69.7; 435/252.3; 435/325; 435/320.1; 536/23.4; 536/23.5

[58] Field of Search ............................... 435/69.1, 252.3, 435/325, 320.1, 69.7; 536/23.4, 23.5

[56] References Cited

U.S. PATENT DOCUMENTS

| | | | |
|---|---|---|---|
| 5,013,649 | 5/1991 | Wang et al. | 435/69.1 |
| 5,071,834 | 12/1991 | Burton et al. | 514/12 |
| 5,106,748 | 4/1992 | Wozney et al. | 435/252.3 |
| 5,108,922 | 4/1992 | Wang et al. | 435/240.2 |
| 5,116,738 | 5/1992 | Wang et al. | 435/69.1 |
| 5,141,905 | 8/1992 | Rosen et al. | 435/69.1 |
| 5,166,322 | 11/1992 | Shaw et al. | 530/351 |
| 5,187,076 | 2/1993 | Wozney et al. | 435/69.1 |
| 5,679,783 | 10/1997 | DeRobertis et al. | |

FOREIGN PATENT DOCUMENTS

| | | |
|---|---|---|
| WO 91/18098 | 11/1991 | WIPO . |
| WO 93/00432 | 1/1993 | WIPO . |
| WO 93/16099 | 8/1993 | WIPO . |
| WO 94/01557 | 1/1994 | WIPO . |
| WO 94/15949 | 7/1994 | WIPO . |
| WO 94/15965 | 7/1994 | WIPO . |
| WO 94/15966 | 7/1994 | WIPO . |
| WO 94/21681 | 9/1994 | WIPO . |
| WO 94/26892 | 11/1994 | WIPO . |
| WO 94/26893 | 11/1994 | WIPO . |
| WO 95/01801 | 1/1995 | WIPO . |
| WO 95/01802 | 1/1995 | WIPO . |
| WO 95/10539 | 4/1995 | WIPO . |
| WO 95/16035 | 6/1995 | WIPO . |
| WO 96/01845 | 1/1996 | WIPO . |
| WO 96/02559 | 2/1996 | WIPO . |

OTHER PUBLICATIONS

Wozney et al. "Bone Morphogenetic Proteins". Chapter 20, In, Handbook of Experimental Pharmacology, vol. 107 Physiology and Pharmacology of Bone (eds., G.R. Mundy and T.J. Martin), pp. 725–748, Springer–Verlag, Heidelberg, 1993.
Celeste et al. Identification of transforming growth factor . beta. family members present in bone–inductive protein purified from bovine bone. Proc. Natl. Acad. Sci. U. S. A. (1990), 87(24), 9843–7, Dec. 1990.
DeRobertis and Sasai, Nature 380:37 (1996).
Sasai et al., Nature 376:333 (1995).
Sasai et al., Cell 79:779 (1994).
LaVallie et al., Bio/Technology 11:187 (1993).
Jing et al., Cell 85:1113 (1996).
Treanor et al., Nature 382:80 (1996).
Piccolo et al., Cell 86:589 (1996).
Jones et al., Mol. Endocrinol 6:1961 (1992).
Toyoshima et al., PNAS USA 90:5404 (1993).
Partanen et al., Mol. Cell Biol. 12:1698 (1992).
Crossier et al., Growth Factors 11:137 (1994).
Graham et al., Cell Growth and Differentiation 5:647 (1994).
Morris et al., Science 263:1281 (1994).
Masiakowski and Carroll, J. Biol. Chem. 267:26181 (1992).
Valenzuela et al., Neuron 15:573 (1995).
Tamagnone et al., Oncogene 8:2009 (1993).
Paul et al., Int. J. Cell Cloning 10:309 (1992).
Ganju et al., Oncogene 11:281 (1995).
Karn et al., Oncogene 8:3443 (1993).
Johnson et al., PNAS USA 90:5677 (1993).
Broxmeyer et al., PNAS USA 85:9052 (1988).
Eto et al., Biochem. Biophys. Res. Comm. 142:1095 (1987).
Matzuk et al., Nature 360:313 (1992).
Ogawa et al., J. Biol. Chem. 267:14233 (1992).
Thies et al., J. Bone & Min. Res. 5:305 (1990).
Thies et al., Endocrinology 130:1318 (1992).
Fukui et al., Developmental Biology 159:131 (1993).
Krummen et al., Endocrinology 132:431 (1993).
Vaughn and Vale, Endocrinology 132:2038 (1993).

*Primary Examiner*—Elizabeth C. Kemmerer
*Assistant Examiner*—David S. Romeo
*Attorney, Agent, or Firm*—Steven R. Lazar

[57] ABSTRACT

Purified chordin proteins and processes for producing them are disclosed. DNA molecules encoding the chordin proteins are also disclosed. The proteins may be used in the treatment of bone, cartilage, other connective tissue defects and disorders, including tendon, ligament and meniscus, in wound healing and related tissue repair, as well as for treatment of disorders and defects to tissues which include epidermis, nerve, muscle, including cardiac muscle, and other tissues and wounds, and organs such as liver, brain, lung, cardiac, pancreas and kidney tissue. The proteins may also be useful for the induction inhibition of growth and/or differentiation of undifferentiated embryonic and stem cells. The proteins may be complexed with other proteins, particularly members of the transforming growth factor-beta superfamily of proteins.

12 Claims, No Drawings

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 4425 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GCGGCCGCCC   GACGAGCCCC   TCGCGGCACT   GCCCCGGCCC   CGGCCCCGGC   CCCGGCCCCC       60

TCCGCCGCA    CCGCCCCCGG   CCCGGCCCTC   CGCCCTCCGC   ACTCCCGCCT   CCCTCCCTCC      120

GCCCGCTCCC   GCGCCCTCCT   CCCTCCCTCC   TCCCCAGCTG   TCCCGTTCGC   GTCATGCCGA      180

GCCTCCCGGC   CCCGCCGGCC   CCGCTGCTGC   TCCTCGGGCT   GCTGCTGCTC   GGCTCCCGGC      240

CGGCCCGCGG   CGCCGGCCCC   GAGCCCCCCG   TGCTGCCCAT   CCGTTCTGAG   AAGGAGCCGC      300
```

```
TGCCCGTTCG GGGAGCGGCA GGCTGCACCT TCGGCGGGAA GGTCTATGCC TTGGACGAGA    360
CGTGGCACCC GGACCTAGGG GAGCCATTCG GGGTGATGCG CTGCGTGCTG TGCGCCTGCG    420
AGGCGACAGG GACCTTGAGG CCCAGAGAGA TGAAGTAGCT TGTCTAGGGT CACGCAGCTT    480
CCTCAGTGGG GTCGCCGTAC CAGGGGCCCT GGCAGGGTCA GCTGCAAGAA CATCAAACCA    540
GAGTGCCCAA CCCCGGCCTG TGGGCAGCCG CGCCAGCTGC CGGGACACTG CTGCCAGACC    600
TGCCCCCAGG AGCGCAGCAG TTCGGAGCGG CAGCCGAGCG GCCTGTCCTT CGAGTATCCG    660
CGGGACCCGG AGCATCGCAG TTATAGCGAC CGCGGGGAGC CAGGAGCTGA GGAGCGGGCC    720
CGTGGTGACG GCCACACGGA CTTCGTGGCG CTGCTGACAG GGCCGAGGTC GCAGGCGGTG    780
GCACGAGCCC GAGTCTCGCT GCTGCGCTCT AGCCTCCGCT TCTCTATCTC CTACAGGCGG    840
CTGGACCGCC CTACCAGGAT CCGCTTCTCA GACTCCAATG GCAGTGTCCT GTTTGAGCAC    900
CCTGCAGCCC CCACCCAAGA TGGCCTGGTC TGTGGGGTGT GGCGGGCAGT GCCTCGGTTG    960
TCTCTGCGGC TCCTTAGGGC AGAACAGCTG CATGTGGCAC TTGTGACACT CACTCACCCT   1020
TCAGGGGAGG TCTGGGGGCC TCTCATCCGG CACCGGGCCC TGGCTGCAGA GACCTTCAGT   1080
GCCATCCTGA CTCTAGAAGG CCCCCCACAG CAGGGCGTAG GGGGCATCAC CCTGCTCACT   1140
CTCAGTGACA CAGAGGACTC CTTGCATTTT TTGCTGCTCT TCCGAGGGCT GCTGGAACCC   1200
AGGAGTGGGG GACTAACCCA GGTTCCCTTG AGGCTCCAGA TTCTACACCA GGGGCAGCTA   1260
CTGCGAGAAC TTCAGGCCAA TGTCTCAGCC CAGGAACCAG GCTTTGCTGA GGTGCTGCCC   1320
AACCTGACAG TCCAGGAGAT GGACTGGCTG GTGCTGGGGG AGCTGCAGAT GGCCCTGGAG   1380
TGGGCAGGCA GGCCAGGGCT GCGCATCAGT GGACACATTG CTGCCAGGAA GAGCTGCGAC   1440
GTCCTGCAAA GTGTCCTTTG TGGGGCTGAT GCCCTGATCC CAGTCCAGAC GGGTGCTGCC   1500
GGCTCAGCCA GCCTCACGCT GCTAGGAAAT GGCTCCCTGA TCTATCAGGT GCAAGTGGTA   1560
GGGACAAGCA GTGAGGTGGT GGCCATGACA CTGGAGACCA AGCCTCAGCG GAGGGATCAG   1620
CGCACTGTCC TGTGCCACAT GGCTGGACTC CAGCCAGGAG GACACACGGC CGTGGGTATC   1680
TGCCCTGGGC TGGGTGCCCG AGGGGCTCAT ATGCTGCTGC AGAATGAGCT CTTCCTGAAC   1740
GTGGGCACCA AGGACTTCCC AGACGGAGAG CTTCGGGGGC ACGTGGCTGC CCTGCCCTAC   1800
TGTGGGCATA GCGCCCGCCA TGACACGCTG CCCGTGCCCC TAGCAGGAGC CCTGGTGCTA   1860
CCCCCTGTGA AGAGCCAAGC AGCAGGGCAC GCCTGGCTTT CCTTGGATAC CCACTGTCAC   1920
CTGCACTATG AAGTGCTGCT GGCTGGGCTT GGTGGCTCAG AACAAGGCAC TGTCACTGCC   1980
CACCTCCTTG GGCCTCCTGG AACGCCAGGG CCTCGGCGGC TGCTGAAGGG ATTCTATGGC   2040
TCAGAGGCCC AGGGTGTGGT GAAGGACCTG GAGCCGGAAC TGCTGCGGCA CCTGGCAAAA   2100
GGCATGGCCT CCCTGATGAT CACCACCAAG GGTAGCCCCA GAGGGGAGCT CCGAGGGCAG   2160
GTGCACATAG CCAACCAATG TGAGGTTGGC GGACTGCGCC TGGAGGCGGC CGGGGCCGAG   2220
GGGGTGCGGG CGCTGGGGGC TCCGGATACA GCCTCTGCTG CGCCGCCTGT GGTGCCTGGT   2280
CTCCCGGCCC TAGCGCCCGC CAAACCTGGT GGTCCTGGGC GGCCCCGAGA CCCCAACACA   2340
TGCTTCTTCG AGGGGCAGCA GCGCCCCCAC GGGGCTCGCT GGGCGCCCAA CTACGACCCG   2400
CTCTGCTCAC TCTGCACCTG CCAGAGACGA ACGGTGATCT GTGACCGGGT GGTGTGCCCA   2460
CCGCCCAGCT GCCCACACCC GGTGCAGGCT CCCGACCAGT GCTGCCCTGT TTGCCCTGAG   2520
AAACAAGATG TCAGAGACTT GCCAGGGCTG CCAAGGAGCC GGGACCCAGG AGAGGGCTGC   2580
TATTTTGATG GTGACCGGAG CTGGCGGGCA GCGGGTACGC GGTGGCACCC CGTTGTGCCC   2640
CCCTTTGGCT TAATTAAGTG TGCTGTCTGC ACCTGCAAGG GGGGCACTGG AGAGGTGCAC   2700
```

-continued

| | | | | | |
|---|---|---|---|---|---|
| TGTGAGAAGG | TGCAGTGTCC | CCGGCTGGCC | TGTGCCCAGC | CTGTGCGTGT | CAACCCCACC | 2760
| GACTGCTGCA | AACAGTGTCC | AGTGGGGTCG | GGGGCCCACC | CCCAGCTGGG | GGACCCCATG | 2820
| CAGGCTGATG | GGCCCCGGGG | CTGCCGTTTT | GCTGGGCAGT | GGTTCCCAGA | GAGTCAGAGC | 2880
| TGGCACCCCT | CAGTGCCCCC | TTTTGGAGAG | ATGAGCTGTA | TCACCTGCAG | ATGTGGGCA | 2940
| GGGGTGCCTC | ACTGTGAGCG | GGATGACTGT | TCACTGCCAC | TGTCCTGTGG | CTCGGGGAAG | 3000
| GAGAGTCGAT | GCTGTTCCCG | CTGCACGGCC | CACCGGCGGC | CCCCAGAGAC | CAGAACTGAT | 3060
| CCAGAGCTGG | AGAAAGAAGC | CGAAGGCTCT | TAGGGAGCAG | CCAGAGGGCC | AAGTGACCAA | 3120
| GAGGATGGGG | CCTGAGCTGG | GGAAGGGGTG | GCATCGAGGA | CCTTCTTGCA | TTCTCCTGTG | 3180
| GGAAGCCCAG | TGCCTTTGCT | CCTCTGTCCT | GCCTCTACTC | CCACCCCCAC | TACCTCTGGG | 3240
| AACCACAGCT | CCACAAGGGG | GAGAGGCAGC | TGGGCCAGAC | CGAGGTCACA | GCCACTCCAA | 3300
| GTCCTGCCCT | GCCACCCTCG | GCCTCTGTCC | TGGAAGCCCC | ACCCCTTTCC | TCCTGTACAT | 3360
| AATGTCACTG | GCTTGTTGGG | ATTTTTAATT | TATCTTCACT | CAGCACCAAG | GGCCCCGAC | 3420
| ACTCCACTCC | TGCTGCCCCT | GAGCTGAGCA | GAGTCATTAT | TGGAGAGTTT | TGTATTTATT | 3480
| AAAACATTTC | TTTTTCAGTC | AAAAAAAAAA | AAAATCCCGA | TTGTAACTAT | TATGAGTCCT | 3540
| AGTTGACTTG | AAGTGGAGAA | GGCTACGATT | TTTTTGATGT | CATTTTGTGT | AAGGGCGCAG | 3600
| ACTGCTGCGA | ACAGAGTGGT | GATAGCGCCT | AAGCATAGTG | TTAGAGTTTG | GATTAGTGGG | 3660
| CTATTTCTG | CTAGGGGGTG | GAAGCGGATG | AGTAAGAAGA | TTCCTGCTAC | AACTATAGTG | 3720
| CTTGAGTGGA | GTAGGGCTGA | GACTGGGGTG | GGGCCTTCTA | TGGCTGAGGG | GAGTCAGGGG | 3780
| TGGAGACCTA | ATTGGGCTGA | TTTGCCTGCT | GCTGCTAGGA | GGAGGCCTAG | TAGTGGGGTG | 3840
| AGGCTTGGAT | TAGCGTTTAG | AAGGGCTATT | TGTTGTGGGT | CTCATGAGTT | GGAGTGTAGG | 3900
| ATAAATCATG | CTAAGGCGAG | GATGAAACCG | ATATCGCCGA | TACGGTTGTA | TAGGATTGCT | 3960
| TGAATGGCTG | CTGTGTTGGC | ATCTGCTCGG | GCGTATCATC | AACTGATGAG | CAAGAAGGAT | 4020
| ATAATTCCTA | CGCCCTCTCA | GCCGATGAAC | AGTTGGAATA | GGTTGTTAGC | GGTAACTAAG | 4080
| ATTAGTATGG | TAATTAGGAA | GATGAGTAGA | TATTTGAAGA | ACTGATTAAT | GTTTGGGTCT | 4140
| GAGTTTATAT | ATCACAGTGA | GAATTCTATG | ATGGACCATG | TAACGAACAA | TGCTACAGGG | 4200
| ATGAATATTA | TGGAGAAGTA | GTCTAGTTTG | AAGCTTAGGG | AGAGCTGGGT | TGTTTGGGTT | 4260
| GTGGCTCAGT | GTCAGTTCGA | GATAATAACT | TCTTGGTCTA | GGCACATGAA | TATTGTTGTG | 4320
| GGGAAGAGAC | TGATAATAAA | GGTGGATGCG | ACAATGGATT | TTACATAATG | GGGGTATGAG | 4380
| TTTTTTTTGT | TAGGGTTAAC | GAGGGTAGGC | CTCTTTGGCC | GAATT | | 4425

( 2 ) INFORMATION FOR SEQ ID NO:2:

( i ) SEQUENCE CHARACTERISTICS:
        ( A ) LENGTH: 2865 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..2862

( x i ) SEQUENCE DESCRIPTION: SEQ ID NO:2:

| ATG | CCG | AGC | CTC | CCG | GCC | CCG | CCG | GCC | CCG | CTG | CTG | CTC | CTC | GGG | CTG | 48 |
|---|---|---|---|---|---|---|---|---|---|---|---|---|---|---|---|---|
| Met | Pro | Ser | Leu | Pro | Ala | Pro | Pro | Ala | Pro | Leu | Leu | Leu | Leu | Gly | Leu | |
| 1 | | 5 | | | | 10 | | | | | 15 | | | | | |

| | | | | | | | | | | | | | | | | |
|---|---|---|---|---|---|---|---|---|---|---|---|---|---|---|---|---|
| CTG | CTG | CTC | GGC | TCC | CGG | CCG | GCC | CGC | GGC | GCC | GGC | CCC | GAG | CCC | CCC | 96 |
| Leu | Leu | Leu | Gly | Ser | Arg | Pro | Ala | Arg | Gly | Ala | Gly | Pro | Glu | Pro | Pro | |
| | | | 20 | | | | 25 | | | | | 30 | | | | |
| GTG | CTG | CCC | ATC | CGT | TCT | GAG | AAG | GAG | CCG | CTG | CCC | GTT | CGG | GGA | GCG | 144 |
| Val | Leu | Pro | Ile | Arg | Ser | Glu | Lys | Glu | Pro | Leu | Pro | Val | Arg | Gly | Ala | |
| | | 35 | | | | 40 | | | | | 45 | | | | | |
| GCA | GGC | TGC | ACC | TTC | GGC | GGG | AAG | GTC | TAT | GCC | TTG | GAC | GAG | ACG | TGG | 192 |
| Ala | Gly | Cys | Thr | Phe | Gly | Gly | Lys | Val | Tyr | Ala | Leu | Asp | Glu | Thr | Trp | |
| | 50 | | | | | 55 | | | | | 60 | | | | | |
| CAC | CCG | GAC | CTA | GGG | GAG | CCA | TTC | GGG | GTG | ATG | CGC | TGC | GTG | CTG | TGC | 240 |
| His | Pro | Asp | Leu | Gly | Glu | Pro | Phe | Gly | Val | Met | Arg | Cys | Val | Leu | Cys | |
| 65 | | | | | 70 | | | | | 75 | | | | | 80 | |
| GCC | TGC | GAG | GCG | CCT | CAG | TGG | GGT | CGC | CGT | ACC | AGG | GGC | CCT | GGC | AGG | 288 |
| Ala | Cys | Glu | Ala | Pro | Gln | Trp | Gly | Arg | Arg | Thr | Arg | Gly | Pro | Gly | Arg | |
| | | | | 85 | | | | | 90 | | | | | 95 | | |
| GTC | AGC | TGC | AAG | AAC | ATC | AAA | CCA | GAG | TGC | CCA | ACC | CCG | GCC | TGT | GGG | 336 |
| Val | Ser | Cys | Lys | Asn | Ile | Lys | Pro | Glu | Cys | Pro | Thr | Pro | Ala | Cys | Gly | |
| | | | 100 | | | | 105 | | | | | 110 | | | | |
| CAG | CCG | CGC | CAG | CTG | CCG | GGA | CAC | TGC | TGC | CAG | ACC | TGC | CCC | CAG | GAG | 384 |
| Gln | Pro | Arg | Gln | Leu | Pro | Gly | His | Cys | Cys | Gln | Thr | Cys | Pro | Gln | Glu | |
| | | 115 | | | | 120 | | | | | 125 | | | | | |
| CGC | AGC | AGT | TCG | GAG | CGG | CAG | CCG | AGC | GGC | CTG | TCC | TTC | GAG | TAT | CCG | 432 |
| Arg | Ser | Ser | Ser | Glu | Arg | Gln | Pro | Ser | Gly | Leu | Ser | Phe | Glu | Tyr | Pro | |
| | 130 | | | | | 135 | | | | | 140 | | | | | |
| CGG | GAC | CCG | GAG | CAT | CGC | AGT | TAT | AGC | GAC | CGC | GGG | GAG | CCA | GGA | GCT | 480 |
| Arg | Asp | Pro | Glu | His | Arg | Ser | Tyr | Ser | Asp | Arg | Gly | Glu | Pro | Gly | Ala | |
| 145 | | | | | 150 | | | | | 155 | | | | | 160 | |
| GAG | GAG | CGG | GCC | CGT | GGT | GAC | GGC | CAC | ACG | GAC | TTC | GTG | GCG | CTG | CTG | 528 |
| Glu | Glu | Arg | Ala | Arg | Gly | Asp | Gly | His | Thr | Asp | Phe | Val | Ala | Leu | Leu | |
| | | | | 165 | | | | | 170 | | | | | 175 | | |
| ACA | GGG | CCG | AGG | TCG | CAG | GCG | GTG | GCA | CGA | GCC | CGA | GTC | TCG | CTG | CTG | 576 |
| Thr | Gly | Pro | Arg | Ser | Gln | Ala | Val | Ala | Arg | Ala | Arg | Val | Ser | Leu | Leu | |
| | | | 180 | | | | 185 | | | | | 190 | | | | |
| CGC | TCT | AGC | CTC | CGC | TTC | TCT | ATC | TCC | TAC | AGG | CGG | CTG | GAC | CGC | CCT | 624 |
| Arg | Ser | Ser | Leu | Arg | Phe | Ser | Ile | Ser | Tyr | Arg | Arg | Leu | Asp | Arg | Pro | |
| | | 195 | | | | 200 | | | | | 205 | | | | | |
| ACC | AGG | ATC | CGC | TTC | TCA | GAC | TCC | AAT | GGC | AGT | GTC | CTG | TTT | GAG | CAC | 672 |
| Thr | Arg | Ile | Arg | Phe | Ser | Asp | Ser | Asn | Gly | Ser | Val | Leu | Phe | Glu | His | |
| | 210 | | | | | 215 | | | | | 220 | | | | | |
| CCT | GCA | GCC | CCC | ACC | CAA | GAT | GGC | CTG | GTC | TGT | GGG | GTG | TGG | CGG | GCA | 720 |
| Pro | Ala | Ala | Pro | Thr | Gln | Asp | Gly | Leu | Val | Cys | Gly | Val | Trp | Arg | Ala | |
| 225 | | | | | 230 | | | | | 235 | | | | | 240 | |
| GTG | CCT | CGG | TTG | TCT | CTG | CGG | CTC | CTT | AGG | GCA | GAA | CAG | CTG | CAT | GTG | 768 |
| Val | Pro | Arg | Leu | Ser | Leu | Arg | Leu | Leu | Arg | Ala | Glu | Gln | Leu | His | Val | |
| | | | | 245 | | | | | 250 | | | | | 255 | | |
| GCA | CTT | GTG | ACA | CTC | ACT | CAC | CCT | TCA | GGG | GAG | GTC | TGG | GGG | CCT | CTC | 816 |
| Ala | Leu | Val | Thr | Leu | Thr | His | Pro | Ser | Gly | Glu | Val | Trp | Gly | Pro | Leu | |
| | | | 260 | | | | 265 | | | | | 270 | | | | |
| ATC | CGG | CAC | CGG | GCC | CTG | GCT | GCA | GAG | ACC | TTC | AGT | GCC | ATC | CTG | ACT | 864 |
| Ile | Arg | His | Arg | Ala | Leu | Ala | Ala | Glu | Thr | Phe | Ser | Ala | Ile | Leu | Thr | |
| | | 275 | | | | 280 | | | | | 285 | | | | | |
| CTA | GAA | GGC | CCC | CCA | CAG | CAG | GGC | GTA | GGG | GGC | ATC | ACC | CTG | CTC | ACT | 912 |
| Leu | Glu | Gly | Pro | Pro | Gln | Gln | Gly | Val | Gly | Gly | Ile | Thr | Leu | Leu | Thr | |
| | 290 | | | | | 295 | | | | | 300 | | | | | |
| CTC | AGT | GAC | ACA | GAG | GAC | TCC | TTG | CAT | TTT | TTG | CTG | CTC | TTC | CGA | GGG | 960 |
| Leu | Ser | Asp | Thr | Glu | Asp | Ser | Leu | His | Phe | Leu | Leu | Leu | Phe | Arg | Gly | |
| 305 | | | | | 310 | | | | | 315 | | | | | 320 | |
| CTG | CTG | GAA | CCC | AGG | AGT | GGG | GGA | CTA | ACC | CAG | GTT | CCC | TTG | AGG | CTC | 1008 |
| Leu | Leu | Glu | Pro | Arg | Ser | Gly | Gly | Leu | Thr | Gln | Val | Pro | Leu | Arg | Leu | |
| | | | | 325 | | | | | 330 | | | | | 335 | | |

-continued

| | | | | | | | | | | | | | | | | |
|---|---|---|---|---|---|---|---|---|---|---|---|---|---|---|---|---|
| CAG | ATT | CTA | CAC | CAG | GGG | CAG | CTA | CTG | CGA | GAA | CTT | CAG | GCC | AAT | GTC | 1056 |
| Gln | Ile | Leu | His | Gln | Gly | Gln | Leu | Leu | Arg | Glu | Leu | Gln | Ala | Asn | Val | |
| | | | 340 | | | | 345 | | | | | | 350 | | | |
| TCA | GCC | CAG | GAA | CCA | GGC | TTT | GCT | GAG | GTG | CTG | CCC | AAC | CTG | ACA | GTC | 1104 |
| Ser | Ala | Gln | Glu | Pro | Gly | Phe | Ala | Glu | Val | Leu | Pro | Asn | Leu | Thr | Val | |
| | | 355 | | | | | 360 | | | | | 365 | | | | |
| CAG | GAG | ATG | GAC | TGG | CTG | GTG | CTG | GGG | GAG | CTG | CAG | ATG | GCC | CTG | GAG | 1152 |
| Gln | Glu | Met | Asp | Trp | Leu | Val | Leu | Gly | Glu | Leu | Gln | Met | Ala | Leu | Glu | |
| 370 | | | | | 375 | | | | | 380 | | | | | | |
| TGG | GCA | GGC | AGG | CCA | GGG | CTG | CGC | ATC | AGT | GGA | CAC | ATT | GCT | GCC | AGG | 1200 |
| Trp | Ala | Gly | Arg | Pro | Gly | Leu | Arg | Ile | Ser | Gly | His | Ile | Ala | Ala | Arg | |
| 385 | | | | | 390 | | | | 395 | | | | | | 400 | |
| AAG | AGC | TGC | GAC | GTC | CTG | CAA | AGT | GTC | CTT | TGT | GGG | GCT | GAT | GCC | CTG | 1248 |
| Lys | Ser | Cys | Asp | Val | Leu | Gln | Ser | Val | Leu | Cys | Gly | Ala | Asp | Ala | Leu | |
| | | | | 405 | | | | | 410 | | | | | 415 | | |
| ATC | CCA | GTC | CAG | ACG | GGT | GCT | GCC | GGC | TCA | GCC | AGC | CTC | ACG | CTG | CTA | 1296 |
| Ile | Pro | Val | Gln | Thr | Gly | Ala | Ala | Gly | Ser | Ala | Ser | Leu | Thr | Leu | Leu | |
| | | | 420 | | | | | 425 | | | | | 430 | | | |
| GGA | AAT | GGC | TCC | CTG | ATC | TAT | CAG | GTG | CAA | GTG | GTA | GGG | ACA | AGC | AGT | 1344 |
| Gly | Asn | Gly | Ser | Leu | Ile | Tyr | Gln | Val | Gln | Val | Val | Gly | Thr | Ser | Ser | |
| | | 435 | | | | | 440 | | | | | 445 | | | | |
| GAG | GTG | GTG | GCC | ATG | ACA | CTG | GAG | ACC | AAG | CCT | CAG | CGG | AGG | GAT | CAG | 1392 |
| Glu | Val | Val | Ala | Met | Thr | Leu | Glu | Thr | Lys | Pro | Gln | Arg | Arg | Asp | Gln | |
| 450 | | | | | 455 | | | | | 460 | | | | | | |
| CGC | ACT | GTC | CTG | TGC | CAC | ATG | GCT | GGA | CTC | CAG | CCA | GGA | GGA | CAC | ACG | 1440 |
| Arg | Thr | Val | Leu | Cys | His | Met | Ala | Gly | Leu | Gln | Pro | Gly | Gly | His | Thr | |
| 465 | | | | | 470 | | | | | 475 | | | | | 480 | |
| GCC | GTG | GGT | ATC | TGC | CCT | GGG | CTG | GGT | GCC | CGA | GGG | GCT | CAT | ATG | CTG | 1488 |
| Ala | Val | Gly | Ile | Cys | Pro | Gly | Leu | Gly | Ala | Arg | Gly | Ala | His | Met | Leu | |
| | | | | 485 | | | | | 490 | | | | | 495 | | |
| CTG | CAG | AAT | GAG | CTC | TTC | CTG | AAC | GTG | GGC | ACC | AAG | GAC | TTC | CCA | GAC | 1536 |
| Leu | Gln | Asn | Glu | Leu | Phe | Leu | Asn | Val | Gly | Thr | Lys | Asp | Phe | Pro | Asp | |
| | | | 500 | | | | | 505 | | | | | 510 | | | |
| GGA | GAG | CTT | CGG | GGG | CAC | GTG | GCT | GCC | CTG | CCC | TAC | TGT | GGG | CAT | AGC | 1584 |
| Gly | Glu | Leu | Arg | Gly | His | Val | Ala | Ala | Leu | Pro | Tyr | Cys | Gly | His | Ser | |
| | | 515 | | | | | 520 | | | | | 525 | | | | |
| GCC | CGC | CAT | GAC | ACG | CTG | CCC | GTG | CCC | CTA | GCA | GGA | GCC | CTG | GTG | CTA | 1632 |
| Ala | Arg | His | Asp | Thr | Leu | Pro | Val | Pro | Leu | Ala | Gly | Ala | Leu | Val | Leu | |
| | 530 | | | | | 535 | | | | | 540 | | | | | |
| CCC | CCT | GTG | AAG | AGC | CAA | GCA | GCA | GGG | CAC | GCC | TGG | CTT | TCC | TTG | GAT | 1680 |
| Pro | Pro | Val | Lys | Ser | Gln | Ala | Ala | Gly | His | Ala | Trp | Leu | Ser | Leu | Asp | |
| 545 | | | | | 550 | | | | | 555 | | | | | 560 | |
| ACC | CAC | TGT | CAC | CTG | CAC | TAT | GAA | GTG | CTG | CTG | GCT | GGG | CTT | GGT | GGC | 1728 |
| Thr | His | Cys | His | Leu | His | Tyr | Glu | Val | Leu | Leu | Ala | Gly | Leu | Gly | Gly | |
| | | | | 565 | | | | | 570 | | | | | 575 | | |
| TCA | GAA | CAA | GGC | ACT | GTC | ACT | GCC | CAC | CTC | CTT | GGG | CCT | CCT | GGA | ACG | 1776 |
| Ser | Glu | Gln | Gly | Thr | Val | Thr | Ala | His | Leu | Leu | Gly | Pro | Pro | Gly | Thr | |
| | | | 580 | | | | | 585 | | | | | 590 | | | |
| CCA | GGG | CCT | CGG | CGG | CTG | CTG | AAG | GGA | TTC | TAT | GGC | TCA | GAG | GCC | CAG | 1824 |
| Pro | Gly | Pro | Arg | Arg | Leu | Leu | Lys | Gly | Phe | Tyr | Gly | Ser | Glu | Ala | Gln | |
| | | 595 | | | | | 600 | | | | | 605 | | | | |
| GGT | GTG | GTG | AAG | GAC | CTG | GAG | CCG | GAA | CTG | CTG | CGG | CAC | CTG | GCA | AAA | 1872 |
| Gly | Val | Val | Lys | Asp | Leu | Glu | Pro | Glu | Leu | Leu | Arg | His | Leu | Ala | Lys | |
| | 610 | | | | | 615 | | | | | 620 | | | | | |
| GGC | ATG | GCC | TCC | CTG | ATG | ATC | ACC | ACC | AAG | GGT | AGC | CCC | AGA | GGG | GAG | 1920 |
| Gly | Met | Ala | Ser | Leu | Met | Ile | Thr | Thr | Lys | Gly | Ser | Pro | Arg | Gly | Glu | |
| 625 | | | | | 630 | | | | | 635 | | | | | 640 | |
| CTC | CGA | GGG | CAG | GTG | CAC | ATA | GCC | AAC | CAA | TGT | GAG | GTT | GGC | GGA | CTG | 1968 |
| Leu | Arg | Gly | Gln | Val | His | Ile | Ala | Asn | Gln | Cys | Glu | Val | Gly | Gly | Leu | |
| | | | | 645 | | | | | 650 | | | | | 655 | | |

| | | | | | | | | | | | | | | | | |
|---|---|---|---|---|---|---|---|---|---|---|---|---|---|---|---|---|
| CGC | CTG | GAG | GCG | GCC | GGG | GCC | GAG | GGG | GTG | CGG | GCG | CTG | GGG | GCT | CCG | 2016 |
| Arg | Leu | Glu | Ala | Ala | Gly | Ala | Glu | Gly | Val | Arg | Ala | Leu | Gly | Ala | Pro | |
| | | | 660 | | | | 665 | | | | | 670 | | | | |
| GAT | ACA | GCC | TCT | GCT | GCG | CCG | CCT | GTG | GTG | CCT | GGT | CTC | CCG | GCC | CTA | 2064 |
| Asp | Thr | Ala | Ser | Ala | Ala | Pro | Pro | Val | Val | Pro | Gly | Leu | Pro | Ala | Leu | |
| | | 675 | | | | 680 | | | | | 685 | | | | | |
| GCG | CCC | GCC | AAA | CCT | GGT | GGT | CCT | GGG | CGG | CCC | CGA | GAC | CCC | AAC | ACA | 2112 |
| Ala | Pro | Ala | Lys | Pro | Gly | Gly | Pro | Gly | Arg | Pro | Arg | Asp | Pro | Asn | Thr | |
| | 690 | | | | | 695 | | | | | 700 | | | | | |
| TGC | TTC | TTC | GAG | GGG | CAG | CAG | CGC | CCC | CAC | GGG | GCT | CGC | TGG | GCG | CCC | 2160 |
| Cys | Phe | Phe | Glu | Gly | Gln | Gln | Arg | Pro | His | Gly | Ala | Arg | Trp | Ala | Pro | |
| 705 | | | | | 710 | | | | | 715 | | | | | 720 | |
| AAC | TAC | GAC | CCG | CTC | TGC | TCA | CTC | TGC | ACC | TGC | CAG | AGA | CGA | ACG | GTG | 2208 |
| Asn | Tyr | Asp | Pro | Leu | Cys | Ser | Leu | Cys | Thr | Cys | Gln | Arg | Arg | Thr | Val | |
| | | | | 725 | | | | | 730 | | | | | 735 | | |
| ATC | TGT | GAC | CCG | GTG | GTG | TGC | CCA | CCG | CCC | AGC | TGC | CCA | CAC | CCG | GTG | 2256 |
| Ile | Cys | Asp | Pro | Val | Val | Cys | Pro | Pro | Pro | Ser | Cys | Pro | His | Pro | Val | |
| | | | 740 | | | | | 745 | | | | | 750 | | | |
| CAG | GCT | CCC | GAC | CAG | TGC | TGC | CCT | GTT | TGC | CCT | GAG | AAA | CAA | GAT | GTC | 2304 |
| Gln | Ala | Pro | Asp | Gln | Cys | Cys | Pro | Val | Cys | Pro | Glu | Lys | Gln | Asp | Val | |
| | | 755 | | | | 760 | | | | | 765 | | | | | |
| AGA | GAC | TTG | CCA | GGG | CTG | CCA | AGG | AGC | CGG | GAC | CCA | GGA | GAG | GGC | TGC | 2352 |
| Arg | Asp | Leu | Pro | Gly | Leu | Pro | Arg | Ser | Arg | Asp | Pro | Gly | Glu | Gly | Cys | |
| | 770 | | | | | 775 | | | | | 780 | | | | | |
| TAT | TTT | GAT | GGT | GAC | CGG | AGC | TGG | CGG | GCA | GCG | GGT | ACG | CGG | TGG | CAC | 2400 |
| Tyr | Phe | Asp | Gly | Asp | Arg | Ser | Trp | Arg | Ala | Ala | Gly | Thr | Arg | Trp | His | |
| 785 | | | | | 790 | | | | | 795 | | | | | 800 | |
| CCC | GTT | GTG | CCC | CCC | TTT | GGC | TTA | ATT | AAG | TGT | GCT | GTC | TGC | ACC | TGC | 2448 |
| Pro | Val | Val | Pro | Pro | Phe | Gly | Leu | Ile | Lys | Cys | Ala | Val | Cys | Thr | Cys | |
| | | | | 805 | | | | | 810 | | | | | 815 | | |
| AAG | GGG | GGC | ACT | GGA | GAG | GTG | CAC | TGT | GAG | AAG | GTG | CAG | TGT | CCC | CGG | 2496 |
| Lys | Gly | Gly | Thr | Gly | Glu | Val | His | Cys | Glu | Lys | Val | Gln | Cys | Pro | Arg | |
| | | | 820 | | | | | 825 | | | | | 830 | | | |
| CTG | GCC | TGT | GCC | CAG | CCT | GTG | CGT | GTC | AAC | CCC | ACC | GAC | TGC | TGC | AAA | 2544 |
| Leu | Ala | Cys | Ala | Gln | Pro | Val | Arg | Val | Asn | Pro | Thr | Asp | Cys | Cys | Lys | |
| | | 835 | | | | 840 | | | | | 845 | | | | | |
| CAG | TGT | CCA | GTG | GGG | TCG | GGG | GCC | CAC | CCC | CAG | CTG | GGG | GAC | CCC | ATG | 2592 |
| Gln | Cys | Pro | Val | Gly | Ser | Gly | Ala | His | Pro | Gln | Leu | Gly | Asp | Pro | Met | |
| | 850 | | | | | 855 | | | | | 860 | | | | | |
| CAG | GCT | GAT | GGG | CCC | CGG | GGC | TGC | CGT | TTT | GCT | GGG | CAG | TGG | TTC | CCA | 2640 |
| Gln | Ala | Asp | Gly | Pro | Arg | Gly | Cys | Arg | Phe | Ala | Gly | Gln | Trp | Phe | Pro | |
| 865 | | | | | 870 | | | | | 875 | | | | | 880 | |
| GAG | AGT | CAG | AGC | TGG | CAC | CCC | TCA | GTG | CCC | CCT | TTT | GGA | GAG | ATG | AGC | 2688 |
| Glu | Ser | Gln | Ser | Trp | His | Pro | Ser | Val | Pro | Pro | Phe | Gly | Glu | Met | Ser | |
| | | | | 885 | | | | | 890 | | | | | 895 | | |
| TGT | ATC | ACC | TGC | AGA | TGT | GGG | GCA | GGG | GTG | CCT | CAC | TGT | GAG | CGG | GAT | 2736 |
| Cys | Ile | Thr | Cys | Arg | Cys | Gly | Ala | Gly | Val | Pro | His | Cys | Glu | Arg | Asp | |
| | | | 900 | | | | | 905 | | | | | 910 | | | |
| GAC | TGT | TCA | CTG | CCA | CTG | TCC | TGT | GGC | TCG | GGG | AAG | GAG | AGT | CGA | TGC | 2784 |
| Asp | Cys | Ser | Leu | Pro | Leu | Ser | Cys | Gly | Ser | Gly | Lys | Glu | Ser | Arg | Cys | |
| | | 915 | | | | 920 | | | | | 925 | | | | | |
| TGT | TCC | CGC | TGC | ACG | GCC | CAC | CGG | CGG | CCC | CCA | GAG | ACC | AGA | ACT | GAT | 2832 |
| Cys | Ser | Arg | Cys | Thr | Ala | His | Arg | Arg | Pro | Pro | Glu | Thr | Arg | Thr | Asp | |
| | 930 | | | | | 935 | | | | | 940 | | | | | |
| CCA | GAG | CTG | GAG | AAA | GAA | GCC | GAA | GGC | TCT | TAG | | | | | | 2865 |
| Pro | Glu | Leu | Glu | Lys | Glu | Ala | Glu | Gly | Ser | | | | | | | |
| 945 | | | | 950 | | | | | | | | | | | | |

( 2 ) INFORMATION FOR SEQ ID NO:3:

( i ) SEQUENCE CHARACTERISTICS:

(A) LENGTH: 954 amino acids
(B) TYPE: amino acid
(D) TOPOLOGY: linear (ii) MOLECULE TYPE: protein (xi) SEQUENCE DESCRIPTION: SEQ ID NO:3:

```
Met Pro Ser Leu Pro Ala Pro Pro Ala Pro Leu Leu Leu Gly Leu
  1               5                  10                  15

Leu Leu Leu Gly Ser Arg Pro Ala Arg Gly Ala Gly Pro Glu Pro Pro
             20                  25                  30

Val Leu Pro Ile Arg Ser Glu Lys Glu Pro Leu Pro Val Arg Gly Ala
         35                  40                  45

Ala Gly Cys Thr Phe Gly Gly Lys Val Tyr Ala Leu Asp Glu Thr Trp
     50                  55                  60

His Pro Asp Leu Gly Glu Pro Phe Gly Val Met Arg Cys Val Leu Cys
 65                  70                  75                  80

Ala Cys Glu Ala Pro Gln Trp Gly Arg Arg Thr Arg Gly Pro Gly Arg
                 85                  90                  95

Val Ser Cys Lys Asn Ile Lys Pro Glu Cys Pro Thr Pro Ala Cys Gly
                100                 105                 110

Gln Pro Arg Gln Leu Pro Gly His Cys Cys Gln Thr Cys Pro Gln Glu
             115                 120                 125

Arg Ser Ser Glu Arg Gln Pro Ser Gly Leu Ser Phe Glu Tyr Pro
     130                 135                 140

Arg Asp Pro Glu His Arg Ser Tyr Ser Asp Arg Gly Glu Pro Gly Ala
145                 150                 155                 160

Glu Glu Arg Ala Arg Gly Asp Gly His Thr Asp Phe Val Ala Leu Leu
                165                 170                 175

Thr Gly Pro Arg Ser Gln Ala Val Ala Arg Ala Arg Val Ser Leu Leu
            180                 185                 190

Arg Ser Ser Leu Arg Phe Ser Ile Ser Tyr Arg Arg Leu Asp Arg Pro
        195                 200                 205

Thr Arg Ile Arg Phe Ser Asp Ser Asn Gly Ser Val Leu Phe Glu His
    210                 215                 220

Pro Ala Ala Pro Thr Gln Asp Gly Leu Val Cys Gly Val Trp Arg Ala
225                 230                 235                 240

Val Pro Arg Leu Ser Leu Arg Leu Leu Arg Ala Glu Gln Leu His Val
                245                 250                 255

Ala Leu Val Thr Leu Thr His Pro Ser Gly Glu Val Trp Gly Pro Leu
            260                 265                 270

Ile Arg His Arg Ala Leu Ala Ala Glu Thr Phe Ser Ala Ile Leu Thr
        275                 280                 285

Leu Glu Gly Pro Pro Gln Gln Gly Val Gly Gly Ile Thr Leu Leu Thr
    290                 295                 300

Leu Ser Asp Thr Glu Asp Ser Leu His Phe Leu Leu Phe Arg Gly
305                 310                 315                 320

Leu Leu Glu Pro Arg Ser Gly Gly Leu Thr Gln Val Pro Leu Arg Leu
                325                 330                 335

Gln Ile Leu His Gln Gly Gln Leu Leu Arg Glu Leu Gln Ala Asn Val
            340                 345                 350

Ser Ala Gln Glu Pro Gly Phe Ala Glu Val Leu Pro Asn Leu Thr Val
        355                 360                 365

Gln Glu Met Asp Trp Leu Val Leu Gly Glu Leu Gln Met Ala Leu Glu
    370                 375                 380
```

-continued

```
Trp  Ala  Gly  Arg  Pro  Gly  Leu  Arg  Ile  Ser  Gly  His  Ile  Ala  Ala  Arg
385                 390                 395                 400

Lys  Ser  Cys  Asp  Val  Leu  Gln  Ser  Val  Leu  Cys  Gly  Ala  Asp  Ala  Leu
                405                 410                 415

Ile  Pro  Val  Gln  Thr  Gly  Ala  Ala  Ser  Ala  Ser  Leu  Thr  Leu  Leu
               420                 425                 430

Gly  Asn  Gly  Ser  Leu  Ile  Tyr  Gln  Val  Gln  Val  Val  Gly  Thr  Ser  Ser
          435                 440                 445

Glu  Val  Val  Ala  Met  Thr  Leu  Glu  Thr  Lys  Pro  Gln  Arg  Arg  Asp  Gln
     450                 455                 460

Arg  Thr  Val  Leu  Cys  His  Met  Ala  Gly  Leu  Gln  Pro  Gly  Gly  His  Thr
465                 470                 475                 480

Ala  Val  Gly  Ile  Cys  Pro  Gly  Leu  Gly  Ala  Arg  Gly  Ala  His  Met  Leu
                485                 490                 495

Leu  Gln  Asn  Glu  Leu  Phe  Leu  Asn  Val  Gly  Thr  Lys  Asp  Phe  Pro  Asp
               500                 505                 510

Gly  Glu  Leu  Arg  Gly  His  Val  Ala  Ala  Leu  Pro  Tyr  Cys  Gly  His  Ser
               515                 520                 525

Ala  Arg  His  Asp  Thr  Leu  Pro  Val  Pro  Leu  Ala  Gly  Ala  Leu  Val  Leu
     530                 535                 540

Pro  Pro  Val  Lys  Ser  Gln  Ala  Ala  Gly  His  Ala  Trp  Leu  Ser  Leu  Asp
545                 550                 555                 560

Thr  His  Cys  His  Leu  His  Tyr  Glu  Val  Leu  Leu  Ala  Gly  Leu  Gly  Gly
               565                 570                 575

Ser  Glu  Gln  Gly  Thr  Val  Thr  Ala  His  Leu  Leu  Gly  Pro  Pro  Gly  Thr
               580                 585                 590

Pro  Gly  Pro  Arg  Arg  Leu  Leu  Lys  Gly  Phe  Tyr  Gly  Ser  Glu  Ala  Gln
               595                 600                 605

Gly  Val  Val  Lys  Asp  Leu  Glu  Pro  Glu  Leu  Leu  Arg  His  Leu  Ala  Lys
610                 615                 620

Gly  Met  Ala  Ser  Leu  Met  Ile  Thr  Thr  Lys  Gly  Ser  Pro  Arg  Gly  Glu
625                 630                 635                 640

Leu  Arg  Gly  Gln  Val  His  Ile  Ala  Asn  Gln  Cys  Glu  Val  Gly  Gly  Leu
               645                 650                 655

Arg  Leu  Glu  Ala  Ala  Gly  Ala  Glu  Gly  Val  Arg  Ala  Leu  Gly  Ala  Pro
               660                 665                 670

Asp  Thr  Ala  Ser  Ala  Ala  Pro  Pro  Val  Val  Pro  Gly  Leu  Pro  Ala  Leu
               675                 680                 685

Ala  Pro  Ala  Lys  Pro  Gly  Gly  Pro  Gly  Arg  Pro  Arg  Asp  Pro  Asn  Thr
               690                 695                 700

Cys  Phe  Phe  Glu  Gly  Gln  Gln  Arg  Pro  His  Gly  Ala  Arg  Trp  Ala  Pro
705                 710                 715                 720

Asn  Tyr  Asp  Pro  Leu  Cys  Ser  Leu  Cys  Thr  Cys  Gln  Arg  Arg  Thr  Val
               725                 730                 735

Ile  Cys  Asp  Pro  Val  Val  Cys  Pro  Pro  Pro  Ser  Cys  Pro  His  Pro  Val
               740                 745                 750

Gln  Ala  Pro  Asp  Gln  Cys  Cys  Pro  Val  Cys  Pro  Glu  Lys  Gln  Asp  Val
               755                 760                 765

Arg  Asp  Leu  Pro  Gly  Leu  Pro  Arg  Ser  Arg  Asp  Pro  Gly  Glu  Gly  Cys
               770                 775                 780

Tyr  Phe  Asp  Gly  Asp  Arg  Ser  Trp  Arg  Ala  Ala  Gly  Thr  Arg  Trp  His
785                 790                 795                 800

Pro  Val  Val  Pro  Pro  Phe  Gly  Leu  Ile  Lys  Cys  Ala  Val  Cys  Thr  Cys
               805                 810                 815
```

```
Lys  Gly  Gly  Thr  Gly  Glu  Val  His  Cys  Glu  Lys  Val  Gln  Cys  Pro  Arg
               820                      825                     830

Leu  Ala  Cys  Ala  Gln  Pro  Val  Arg  Val  Asn  Pro  Thr  Asp  Cys  Cys  Lys
          835                      840                     845

Gln  Cys  Pro  Val  Gly  Ser  Gly  Ala  His  Pro  Gln  Leu  Gly  Asp  Pro  Met
     850                     855                     860

Gln  Ala  Asp  Gly  Pro  Arg  Gly  Cys  Arg  Phe  Ala  Gly  Gln  Trp  Phe  Pro
865                      870                 875                          880

Glu  Ser  Gln  Ser  Trp  His  Pro  Ser  Val  Pro  Pro  Phe  Gly  Glu  Met  Ser
               885                      890                          895

Cys  Ile  Thr  Cys  Arg  Cys  Gly  Ala  Gly  Val  Pro  His  Cys  Glu  Arg  Asp
               900                 905                          910

Asp  Cys  Ser  Leu  Pro  Leu  Ser  Cys  Gly  Ser  Gly  Lys  Glu  Ser  Arg  Cys
          915                      920                     925

Cys  Ser  Arg  Cys  Thr  Ala  His  Arg  Arg  Pro  Pro  Glu  Thr  Arg  Thr  Asp
          930                 935                     940

Pro  Glu  Leu  Glu  Lys  Glu  Ala  Glu  Gly  Ser
945                      950
```

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CCACGTCTCG TCCAAGGCAT AGACCTT                                         27

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CCAGCTCCGG TCACCATCAA AATAGCA                                         27

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CATGGGCAGC TCGAG                                                                15

( 2 ) INFORMATION FOR SEQ ID NO:7:

( i ) SEQUENCE CHARACTERISTICS:
        ( A ) LENGTH: 34 base pairs
        ( B ) TYPE: nucleic acid
        ( C ) STRANDEDNESS: single -continued (D) TOPOLOGY: linear (ii) MOLECULE TYPE: DNA (genomic)

(xi) SEQUENCE DESCRIPTION: SEQ ID NO:7:

CTGCAGGCGA GCCTGAATTC CTCGAGCCAT CATG 34

(2) INFORMATION FOR SEQ ID NO:8:

(i) SEQUENCE CHARACTERISTICS:
(A) LENGTH: 68 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:8:

CGTCTAGGCC CCCCGAACCA CGGGGACGTG GTTTTCCTTT GCGAGGTTAA AAAAAAAAC 60

ACGATTGC 68

DNA MOLECULES ENCODING HUMAN CHORDIN

This application is a continuation-in-part from Ser. No. 343,760, filed on Nov. 22, 1994, and issued as U.S. Pat. No. 5,679,783.

The present invention relates to a novel family of purified proteins designated chordin and related proteins, DNA encoding them, and processes for obtaining them. These proteins may be used to induce and/or regulate bone and/or cartilage or other connective tissue formation, and in wound healing and tissue repair. These proteins may also be used for augmenting the activity of other bone morphogenetic proteins.

BACKGROUND OF THE INVENTION

The search for the molecule or molecules responsible for the bone-, cartilage-, and other connective tissue-inductive activity present in bone and other tissue extracts has led to the discovery and identification of a several groups of molecules, such as the Bone Morphogenetic Proteins (BMPs). The unique inductive activities of these proteins, along with their presence in bone, suggests that they are important regulators of bone repair processes, and may be involved in the normal maintenance of bone tissue. There is a need to identify whether additional proteins, particularly human proteins, exist which play a role in these processes. It has recently been reported that *Xenopus chordin* is a molecule which contributes to dorsoventral patterning by binding to BMP-4. Piccolo et al., *Cell*, 86: 589–98 (1996). The present invention relates to the identification of such a novel human protein, which the inventors have designated human chordin.

Human chordin is the human homolog of a xenopus protein called chordin. The nucleotide and amino acid sequences of *xenopus chordin* are described in Lasai et al., *Cell*, 79: 779–790 (1994). The *xenopus chordin* gene has been described as being expressed in the frog embryo head, trunk and tail organizer regions during gastrulation, and as being capable of inducing secondary axes in frog embryos, and rescuing axis formation in ventralized frog, as well as modifying mesoderm induction. Ibid. In addition, *xenopus chordin* has been shown to induce anterior neural markers in the absence of mesoderm induction. Sashai et al., *Nature*, 376: 333–336 (1995).

SUMMARY OF THE INVENTION

As used herein, the term chordin protein refers to the human chordin protein, having the amino acid sequence specified in SEQUENCE ID NO:3, as well as DNA sequences encoding the chordin protein, such as the native human sequence shown in SEQUENCE ID NO:1. Also included are naturally occurring allelic sequences and synthetic variants of SEQUENCE ID NO:1 and 2, and equivalent degenerative codon sequences of the above.

The chordin DNA sequence (SEQ ID NO: 1) and amino acid sequence (SEQ ID NO: 3) are set forth in the Sequence Listings. Chordin proteins may be capable of binding to BMPs and/or inducing or altering the formation of cartilage, bone, or other connective tissue, or combinations thereof. Thus, chordin proteins may be assayed using BMP binding assays, as described in the examples, as well as the cartilage and bone formation and other assays described below. Chordin proteins may be further characterized by the ability to demonstrate effects upon the growth and/or differentiation of embryonic cells and/or stem cells. Thus, the proteins or compositions of the present invention may also be useful for treating cell populations, such as embryonic cells or stem cell populations, to enhance or enrich the growth and/or differentiation of the cells.

Human chordin protein may be produced by culturing a cell transformed with a DNA sequence comprising nucleotides encoding the mature chordin polypeptide and, in the case of eukaryotic cells, a suitable signal peptide. Such DNA sequences, for example, may comprise nucleotide #1 to nucleotide #4425 as shown in SEQ ID NO: 1, or nucleotide #1, 64, 70 or 79 to #2862 as shown in SEQ ID NO: 2. The protein may be recovered and purified from the culture medium from such transformed cells. Such protein may be characterized by an amino acid sequence comprising amino acids #1, 22, 24 or 27 to #954 as shown in SEQ ID NO: 3 substantially free from other proteinaceous materials with which it is co-produced. For production in mammalian cells, the DNA sequence further comprises a DNA sequence encoding a suitable propeptide 5' to and linked in frame to the nucleotide sequence encoding the mature chordin-related polypeptide. The propeptide may be the native chordin-related propeptide, or may be a propeptide from another protein of a related protein. Where the native chordin propeptide is used, human chordin may be produced by culturing a cell transformed with a DNA sequence comprising a DNA sequence encoding the full chordin polypeptide, comprising nucleotide #1 to #2862 as shown in SEQ ID NO: 2 producing a protein characterized by the amino acid sequence comprising amino acids #1 to #954 as shown in SEQ ID NO: 3, of which amino acids 1 to 23 comprise the native propeptide of human chordin, and recovering and purifying from the culture medium a protein characterized by the amino acid sequence comprising amino acids #24 to #954 as shown in SEQ ID NO: 3, substantially free from other proteinaceous materials with which it is co-produced. It is possible that chordin, as produced in nature, may be a heterologous mixture of proteins with varying N-termini. Potential N-termini of the mature protein include amino acid 22, 24 and 27. Thus, the DNA encoding chordin beginning with nucleotides encoding each of these amino acid residues, and the corresponding peptide sequences, are included in the present invention.

It is expected that other species, particularly human, have DNA sequences homologous to human chordin protein. The invention, therefore, includes methods for obtaining the DNA sequences encoding human chordin protein, the DNA sequences obtained by those methods, and the human protein encoded by those DNA sequences. This method entails utilizing the human chordin protein nucleotide sequence or portions thereof to design probes to screen libraries for the corresponding gene from other species or coding sequences or fragments thereof from using standard techniques. Thus, the present invention may include DNA sequences from other species, which are homologous to human chordin protein and can be obtained using the human chordin sequence. The present invention may also include functional fragments of the human chordin protein, and DNA sequences encoding such functional fragments, as well as functional fragments of other related proteins. The ability of such a fragment to function is determinable by assay of the protein in the biological assays described for the assay of the chordin protein; for example the BMP binding assays described in the examples. A DNA sequence encoding the complete mature human chordin protein (SEQ ID NO: 1 and SEQ ID NO: 2) and the corresponding amino acid sequence (SEQ ID NO: 3) are set forth herein. The chordin proteins of the present invention, such as human chordin, may be produced by culturing a cell transformed with the correlating DNA sequence, such as the human chordin DNA sequence of SEQ ID NO: 2, and recovering and purifying protein, such as human chordin, from the culture medium. The purified expressed protein is substantially free from other proteinaceous materials with which it is co-produced, as well as from other contaminants. The recovered purified protein is contemplated to have the ability to bind to BMPs and hence to exhibit effects on cartilage, bone and/or other connective tissue formation activity. Thus, the proteins of the invention may be further characterized by the ability to demonstrate effects on cartilage, bone and/or other connective tissue formation activity in bone and cartilage formation and other assays described below. Chordin proteins may be further characterized by the ability to demonstrate effects upon the growth and/or differentiation of embryonic cells and/or stem cells. Thus, the proteins or compositions of the present invention may also be characterized by their ability to enhance, enrich or otherwise influence the growth and/or differentiation of the cells.

Another aspect of the invention provides pharmaceutical compositions containing a therapeutically effective amount of human chordin protein, in a pharmaceutically acceptable vehicle or carrier. These compositions of the invention may be used in regulating the formation of bone, cartilage, or other connective tissue, including tendon, ligament, meniscus and other connective tissue, as well as combinations of the above, for example, for regeneration of the tendon-to-bone attachment apparatus. In addition, the compositions of the present invention may be useful for the induction, growth, differentiation, maintenance and/or repair of tissues such as brain, liver, kidney, lung, heart, muscle, epidermis, pancreas, nerve, and other organs. The compositions of the present invention, such as compositions of human chordin, may also be used for wound healing and organ and tissue growth and repair (for example, for ex vivo culture of cells and/or organ cultures).

Compositions of the invention may further include at least one other therapeutically useful agent such as members of the TGF-β superfamily of proteins, which includes BMP proteins BMP-1, BMP-2, BMP-3, BMP-4, BMP-5, BMP-6 and BMP-7, disclosed for instance in U.S. Pat. Nos. 5,108, 922; 5,013,649; 5,116,738; 5,106,748; 5,187,076; and 5,141, 905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in PCT application WO 95/16035; BMP-15, disclosed in co-pending patent application, Ser. No. 08/446,924, filed on May 18, 1995; or BMP-16, disclosed in co-pending patent application, Ser. No. 08/715, 202, filed on Sep. 18, 1996. Other compositions which may also be useful include Vgr-2, Jones et al., *Mol Endocrinol,* 6: 1961–1968 (1992), and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of all of the above applications are hereby incorporated by reference.

It is postulated that chordin's effects may be mediated by interaction with other molecules, such as the TGF-β proteins described above, and may interact with one or more receptor molecules, such as the tyrosine kinase receptors. Thus, the composition of the present invention may comprise a complex comprised of the chordin-related protein of the present invention with one or more other molecules, such as the TGF-β proteins described above. Thus, the present invention includes complexes of chordin polypeptide with at least one polypeptide subunit from a transforming growth factor-beta [TGF-β] superfamily protein member. Further, tyrosine kinase receptor genes and/or proteins, and/or soluble truncated versions thereof, may also be useful in compositions of the present invention, including the following receptors, or soluble truncated versions comprising the extracellular binding domains thereof: LTK, Toyoshima et al., *PNAS USA* 90: 5404 (1993); TIE, Partanen et al., *Mol. Cell Biol* 12: 1698 (1992); DTK, Crosier et al., *Growth Factors* 11: 137 (1994); MER, Graham et al., *Cell Growth and Differentiation* 5: 647 (1994); ALK, Morris et al., *Science* 263: 1281 (1994); RYK, Tamagnone et al., *Oncogene* 8: 2009 (1993); Paul et al., *Int. J Cell Cloning* 10: 309 (1992); ROR1 and ROR2, Masiakowski and Carroll, *J. Biol. Chem.* 267: 26181 (1992); MuSK/Mlk/Nsk2, Valenzuela et al., *Neuron* 15: 573 (1995); Ganju et al., *Oncogene* 11: 281 (1995); TKT, Karn et al., *Oncogene* 8: 3443 (1993); and DDR, Johnson et al., *PNAS USA* 90: 5677 (1993). The disclosure of the above references is hereby incorporated by reference as if reproduced fully herein.

The compositions of the invention may comprise, in addition to a chordin-related protein, other therapeutically useful agents including growth factors such as epidermal growth factor (EGF), fibroblast growth factor (FGF), transforming growth factor (TGF-α and TGF-β), activins, inhibins, and insulin-like growth factor (IGF). The compositions may also include an appropriate matrix for instance, for supporting the composition and providing a surface for bone and/or cartilage and/or other connective tissue growth. The matrix may provide slow release of the osteoinductive protein and/or the appropriate environment for presentation thereof.

The chordin containing compositions may be employed in methods for treating a number of bone and/or cartilage and/or other connective tissue defects, periodontal disease and healing of various types of tissues and wounds. The tissue and wounds which may be treated include epidermis, nerve, muscle, including cardiac muscle, and other tissues and wounds, and other organs such as liver, brain, lung, cardiac, pancreas and kidney tissue. These methods, according to the invention, entail administering to a patient needing bone, cartilage and/or other connective tissue formation, wound healing or tissue repair, an effective amount of a composition comprising chordin protein. The chordin-containing compositions may also be used to treat or prevent such conditions as osteoarthritis, osteoporosis, and other abnormalities of bone, cartilage, muscle, tendon, ligament or other connective tissue, organs such as liver, brain, lung, cardiac, pancreas and kidney tissue, and other tissues. These methods may also entail the administration of a protein of the invention in conjunction with at least one BMP protein or other growth factor as described above. In addition, these methods may also include the administration of a chordin protein with other growth factors including EGF, FGF, TGF-α, TGF-β, activin, inhibin and IGF.

Still a further aspect of the invention are DNA sequences coding for expression of a chordin protein. Such sequences include the sequence of nucleotides in a 5' to 3' direction illustrated in SEQ ID NO: 1 or SEQ ID NO: 2, DNA sequences which, but for the degeneracy of the genetic code, are identical to the DNA sequence SEQ ID NO: 1 or SEQ ID NO: 2, and DNA sequences which encode the protein of SEQ ID NO: 3. Further included in the present invention are DNA sequences which hybridize under stringent conditions with the DNA sequence of SEQ ID NO: 1 or SEQ ID NO: 2 and encode a protein having the ability to influence the formation of cartilage and/or bone and/or other connective tissue, or other organs such as liver, brain, lung, cardiac, pancreas and kidney tissue. Preferred DNA sequences include those which hybridize under stringent conditions [see, T. Maniatis et al, *Molecular Cloning* (*A Laboratory Manual*), Cold Spring Harbor Laboratory (1982), pages 387 to 389]. It is generally preferred that such DNA sequences encode a polypeptide which is at least about 80% homologous, and more preferably at least about 90% homologous, to the mature human chordin amino acid sequence shown in SEQ ID NO: 1 or SEQ ID NO: 2. Finally, allelic or other variations of the sequences of SEQ ID NO: 1 or SEQ ID NO: 2, whether such nucleotide changes result in changes in the peptide sequence or not, but where the peptide sequence still has chordin activity, are also included in the present invention. The present invention also includes fragments of the DNA sequence of chordin shown in SEQ ID NO: 1 or SEQ ID NO: 2 which encode a polypeptide which retains the activity of chordin protein.

The DNA sequences of the present invention are useful, for example, as probes for the detection of mRNA encoding chordin in a given cell population. Thus, the present invention includes methods of detecting or diagnosing genetic disorders involving the chordin gene, or disorders involving cellular, organ or tissue disorders in which chordin is irregularly transcribed or expressed. The DNA sequences may also be useful for preparing vectors for gene therapy applications as described below.

A further aspect of the invention includes vectors comprising a DNA sequence as described above in operative association with an expression control sequence therefor. These vectors may be employed in a novel process for producing a chordin protein of the invention in which a cell line transformed with a DNA sequence encoding a chordin protein in operative association with an expression control sequence therefor, is cultured in a suitable culture medium and a chordin-related protein is recovered and purified therefrom. This process may employ a number of known cells both prokaryotic and eukaryotic as host cells for expression of the polypeptide. The vectors may be used in gene therapy applications. In such use, the vectors may be transfected into the cells of a patient ex vivo, and the cells may be reintroduced into a patient. Alternatively, the vectors may be introduced into a patient in vivo through targeted transfection.

Still a further aspect of the invention are chordin proteins or polypeptides. Such polypeptides are characterized by having an amino acid sequence including the sequence illustrated in SEQ ID NO: 3, variants of the amino acid sequence of SEQ ID NO: 3, including naturally occurring allelic variants, and other variants in which the protein retains the ability to bind to BMPs, and/or the ability to induce, inhibit or influence the formation of cartilage and/or bone and/or other connective tissue, or other organs such as liver, brain, lung, cardiac, pancreas and kidney tissue, or other activity characteristic of chordin. Preferred polypeptides include a polypeptide which is at least about 80% homologous, and more preferably at least about 90% homologous, to the mature human chordin amino acid sequence shown in SEQ ID NO:3. Finally, allelic or other variations of the sequences of SEQ ID NO: 3, whether such amino acid changes are induced by mutagenesis, chemical alteration, or by alteration of DNA sequence used to produce the polypeptide, where the peptide sequence still retains chordin activity, as described in the Examples below, are also included in the present invention. The present invention also includes fragments of the amino acid sequence of chordin shown in SEQ ID NO: 3 which retain the activity of chordin protein, such as the ability to bind to BMPs.

The purified proteins of the present inventions may be used to generate antibodies, either monoclonal or polyclonal, to human chordin and/or other chordin-related proteins, using methods that are known in the art of antibody production. Thus, the present invention also includes antibodies to human chordin and/or other related proteins. The antibodies may be useful for purification of chordin and/or other chordin related proteins, or for inhibiting or preventing the effects of chordin related proteins, or may have agonist effects on cells with BMP receptors. The chordin protein and related proteins may be useful for inducing the growth and/or differentiation of embryonic cells and/or stem cells. Thus, the proteins or compositions of the present invention may also be useful for treating relatively undifferentiated cell populations, such as embryonic cells or stem cell populations, to enhance or enrich the growth and/or differentiation of the cells. The treated cell populations may be useful for implantation and for gene therapy applications.

Description of the Sequences

SEQ ID NO:1 is a nucleotide sequence containing nucleotide sequence encoding the entire mature human chordin polypeptide. This sequence contains an intron which is not naturally translated into protein.

SEQ ID NO: 2 is a nucleotide sequence of human chordin which has been synthetically altered to enhance expression.

SEQ ID NO:3 is the amino acid sequence containing the mature human chordin polypeptide sequence.

SEQ ID NO: 4 is a probe directed to the CR1 repeat of human chordin.

SEQ ID NO: 5 is a probe directed to the CR3 domain of human chordin.

SEQ ID NO: 6 is a recognition site for the restriction endonuclease XhoI.

SEQ ID NO: 7 is a sequence including an XhoI recognition site.

SEQ ID NO: 8 is a portion of the EMC virus leader sequence.

DETAILED DESCRIPTION OF THE INVENTION

The human chordin sequence of the present invention is obtained using the whole or fragments of the *xenopus chordin* DNA sequence, or a partial human chordin sequence, as a probe. Thus, the human chordin DNA sequence comprise the DNA sequence of nucleotides #1 to #4425 of SEQ ID NO: 1. This sequence of the human chordin DNA sequence corresponds well to the *xenopus chordin* DNA sequence described in GenBank accession number L35764. The human chordin protein comprises the sequence of amino acids #1 to 954 of SEQ ID NO: 3. The mature human chordin protein is encoded by nucleotides #70 to #2862 of SEQ ID NO: 1, and comprises the sequence of amino acids #24 to #954 of SEQ ID NO:2. Other active species of human chordin are encoded by nucleotides #1, 64, 70 and 79 to #2862 of SEQ ID NO: 2, and comprise amino acids #1, 22, 24 or 27 to #954 of SEQ ID NO: 3.

It is expected that human chordin protein, as expressed by mammalian cells such as CHO cells, exists as a heterogeneous population of active species of chordin protein with varying N-termini. It is expected that active species will comprise an amino acid sequence beginning with the alanine residue at amino acid #27 of SEQ ID NO:3, or will comprise additional amino acid sequence further in the N-terminal direction. Thus, it is expected that DNA sequences encoding active chordin proteins will comprise a nucleotide sequence comprising nucleotides #1, 64, 70, or 79 to #2862 of SEQ ID NO: 2. Accordingly, active species of human chordin are expected to include those comprising amino acids #1, 22, 24 or 27 to #954 of SEQ ID NO:3.

A host cell may be transformed with a coding sequence encoding a propeptide suitable for the secretion of proteins by the host cell linked in proper reading frame to the coding sequence for the mature chordin protein. For example, see U.S. Pat. No. 5,168,050, in which a DNA encoding a precursor portion of a mammalian protein other than BMP-2 is fused to the DNA encoding a mature BMP-2 protein. See also the specification of WO95/16035, in which the propeptide of BMP-2 is fused to the DNA encoding a mature BMP-12 protein. The disclosure of both of these references are hereby incorporated by reference. Thus, the present invention includes chimeric DNA molecules comprising a DNA sequence encoding a propeptide from a protein, other than human chordin, such as a member of the TGF-β superfamily of proteins, linked in correct reading frame to a DNA sequence encoding human chordin protein, or a related protein. The term "chimeric" is used to signify that the propeptide originates from a different polypeptide than the chordin protein.

The N-terminus of one active species of human chordin is expected to be produced by expression in *E. coli* to be as follows: [M]ARGAGP corresponding to amino acids 24 to 29 of SEQ ID NO:1. Thus, it appears that the N-terminus of this species of chordin is at amino acid #24 of SEQ ID NO: 3, and a DNA sequence encoding said species of chordin would comprise nucleotides #70 to #2862 of SEQ ID NO: 2. The apparent molecular weight of human chordin monomer is expected to be experimentally determined by SDS-PAGE to be approximately 105–110 kd on a Novex 10% tricine gel.

It is expected that other chordin proteins, as expressed by mammalian cells such as CHO cells, also exist as a heterogeneous population of active species of chordin-related protein with varying N-termini. For example, it is expected that active species of human chordin protein will comprise an amino acid sequence beginning with the alanine residue at amino acid #27 of SEQ ID NO:3, or will comprise additional amino acid sequence further in the N-terminal direction. Thus, it is expected that DNA sequences encoding active chordin proteins include those which comprise a nucleotide sequence comprising nucleotides #1, #64, #70 or #79 to #2862 of SEQ ID NO: 2. Accordingly, active human chordin proteins include those comprising amino acids #1, #22, #24 or #27 to #954 of SEQ ID NO: 3, as well as fragments of chordin [such as SEQ 3] which retain chordin activity.

The chordin proteins of the present invention, include polypeptides having a molecular weight of about 105–110 kd, said polypeptide comprising the amino acid sequence of SEQ ID NO: 3 and having the ability to bind to TGF-β and/or BMP proteins, or the ability to alter or influence the formation of cartilage and/or bone and/or other connective tissues, such as exhibited in the embryonic stem cell and Rosen-Modified Sampath-Reddi ectopic implant assays, described in the examples.

The chordin proteins recovered from the culture medium are purified by isolating them from other proteinaceous materials from which they are co-produced and from other contaminants present. Chordin proteins may be characterized by the ability to induce or otherwise influence the formation of cartilage and/or bone and/or other connective tissue and other tissue repair and differentiation, for example, in the embryonic stem cell assay and bone and cartilage formation and other assays, described in the examples below. In addition, chordin proteins may be further characterized by their effects upon the growth and/or differentiation of embryonic cells and/or stem cells. Thus, the proteins or compositions of the present invention may be characterized by the embryonic stem cell assay described below.

The chordin proteins provided herein also include factors encoded by the sequences similar to those of SEQ ID NO: 1 or SEQ ID NO: 2, but into which modifications or deletions are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of SEQ ID NO: 3. These sequences, by virtue of sharing primary, secondary, or tertiary structural and conformational characteristics with bone growth factor polypeptides of SEQ ID NO: 3 may possess biological properties in common therewith. It is know, for example that numerous conservative amino acid substitutions are possible without significantly modifying the structure and conformation of a protein, thus maintaining the biological properties as well. For example, it is recognized that conservative amino acid substitutions may be made among amino acids with basic side chains, such as lysine (Lys or K), arginine (Arg or R) and histidine (His or H); amino acids with acidic side chains, such as aspartic acid (Asp or D) and glutamic acid (Glu or E); amino acids with uncharged polar side chains, such as asparagine (Asn or N), glutamine (Gln or Q), serine (Ser or S), threonine (Thr or T), and tyrosine (Tyr or Y); and amino acids with nonpolar side chains, such as alanine (Ala or A), glycine (Gly or G), valine (Val or V), leucine (Leu or L), isoleucine (Ile or I), proline (Pro or P), phenylalanine (Phe or F), methionine (Met or M), tryptophan (Trp or W) and cysteine (Cys or C). Thus, these modifications and deletions of the native chordin may be employed as biologically active substitutes for naturally-occurring chordin and other polypeptides in therapeutic processes. It can be readily determined whether a given variant of chordin maintains the biological activity of chordin by subjecting both chordin and the variant of chordin to the assays described in the examples.

Other specific mutations of the sequences of chordin proteins described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Additionally, bacterial expression of chordin-related protein will also result in production of a non-glycosylated protein, even if the glycosylation sites are left unmodified.

The present invention also encompasses the novel DNA sequences, free of association with DNA sequences encoding other proteinaceous materials, and coding for expression of chordin proteins. These DNA sequences include those depicted in SEQ ID NO: 1 in a 5' to 3' direction and those sequences which hybridize thereto under stringent hybridization washing conditions [for example, 0.1X SSC, 0.1% SDS at 65° C.; see, T. Maniatis et al, *Molecular Cloning (A Laboratory Manual)*, Cold Spring Harbor Laboratory (1982), pages 387 to 389] and encode a protein having cartilage and/or bone and/or other connective tissue inducing activity. These DNA sequences also include those which comprise the DNA sequence of SEQ ID NO: 1 or SEQ ID NO: 2 and those which hybridize thereto under stringent hybridization conditions and encode a protein which maintain the other activities disclosed for chordin.

Similarly, DNA sequences which code for chordin proteins coded for by the sequences of SEQ ID NO: 1 or SEQ ID NO: 2, or chordin proteins which comprise the amino acid sequence of SEQ ID NO: 3, but which differ in codon sequence due to the degeneracies of the genetic code or allelic variations (naturally-occurring base changes in the species population which may or may not result in an amino acid change) also encode the novel factors described herein. Variations in the DNA sequences of SEQ ID NO: 1 or SEQ ID NO: 2 which are caused by point mutations or by induced modifications (including insertion, deletion, and substitution) to enhance the activity, half-life or production of the polypeptides encoded are also encompassed in the invention.

Another aspect of the present invention provides a novel method for producing chordin proteins. The method of the present invention involves culturing a suitable cell line, which has been transformed with a DNA sequence encoding a chordin protein of the invention, under the control of known regulatory sequences. The transformed host cells are cultured and the chordin proteins recovered and purified from the culture medium. The purified proteins are substantially free from other proteins with which they are co-produced as well as from other contaminants.

Suitable cells or cell lines may be mammalian cells, such as Chinese hamster ovary cells (CHO). The selection of suitable mammalian host cells and methods for transformation, culture, amplification, screening, product production and purification are known in the art. See, e.g., Gething and Sambrook, *Nature*, 293: 620–625 (1981), or alternatively, Kaufman et al, *Mol. Cell. Biol.*, 5(7): 1750–1759 (1985) or Howley et al, U.S. Pat. No. 4,419,446. Another suitable mammalian cell line, which is described in the accompanying examples, is the monkey COS-1 cell line. The mammalian cell CV-1 may also be suitable.

Bacterial cells may also be suitable hosts. For example, the various strains of *E. coli* (e.g., HB101, MC1061) are well-known as host cells in the field of biotechnology. Various strains of *B. subtilis*, Pseudomonas, other bacilli and the like may also be employed in this method. For expression of the protein in bacterial cells, DNA encoding the propeptide of chordin is generally not necessary.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering*, 8: 277–298 (Plenum Press 1986) and references cited therein.

Another aspect of the present invention provides vectors for use in the method of expression of these novel chordin polypeptides. Preferably the vectors contain the full novel DNA sequences described above which encode the novel factors of the invention. Additionally, the vectors contain appropriate expression control sequences permitting expression of the chordin protein sequences. Alternatively, vectors incorporating modified sequences as described above are also embodiments of the present invention. Additionally, the sequence of SEQ ID NO: 1, SEQ ID NO: 2 or other sequences encoding chordin proteins could be manipulated to express a mature chordin protein by deleting chordin propeptide sequences and replacing them with sequences encoding the complete propeptides of other proteins, such as BMP proteins or members of the TGF-β superfamily. Thus, the present invention includes chimeric DNA molecules encoding a propeptide from a protein other than chordin, such as a member of the TGF-β superfamily linked in correct reading frame to a DNA sequence encoding a chordin polypeptide.

The vectors may be employed in the method of transforming cell lines and contain selected regulatory sequences in operative association with the DNA coding sequences of the invention which are capable of directing the replication and expression thereof in selected host cells. Regulatory sequences for such vectors are known to those skilled in the art and may be selected depending upon the host cells. Such selection is routine and does not form part of the present invention.

A protein of the present invention, which induces or influences cartilage and/or bone and/or other connective tissue formation, may have application in the healing of bone fractures and cartilage or other connective tissue defects in humans and other animals. Such a preparation employing a chordin protein may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A chordin-related protein may be used in the treatment of periodontal disease, and in other tooth repair processes. Such agents may provide an environment to attract bone-forming cells, affect or stimulate growth or differentiation of bone-forming cells and their progenitor cells or induce differentiation of progenitors of bone-forming cells, and may also support the regeneration of the periodontal ligament and attachment apparatus, which connects bone and teeth. Chordin polypeptides of the invention may also be useful in the treatment of systemic conditions such as osteoporosis, and under certain circumstances, to augment or inhibit the effects of osteogenic, cartilage-inducing and bone inducing factors. In addition to the TGF-β superfamily of proteins, a variety of osteogenic, cartilage-inducing and bone inducing factors have been described. See, e.g., European patent applications 148,155 and 169,016 for discussions thereof.

The proteins of the invention may also be used in wound healing and related tissue repair. The types of wounds include, but are not limited to burns, incisions and ulcers. (See, e.g. PCT Publication WO84/01106 for discussion of wound healing and related tissue repair). It is further contemplated that proteins of the invention may affect neuronal, astrocytic and glial cell survival and therefore be useful in transplantation and treatment of conditions exhibiting a decrease in neuronal survival and repair. The proteins of the invention may further be useful for the treatment of conditions related to other types of tissue, such as nerve, epidermis, muscle, and other organs such as liver, brain, lung, cardiac, pancreas and kidney tissue. The proteins of the present invention may further be useful for the treatment of relatively undifferentiated cell populations, such as embryonic cells, or stem cells, to enhance growth and/or differentiation of the cells. The proteins of the present invention may also have value as a dietary supplement, or as a component of cell culture media. For this use, the proteins may be used in intact form, or may be predigested to provide a more readily absorbed supplement.

The proteins of the invention may also have other useful properties characteristic of the TGF-β superfamily of proteins. Such properties include angiogenic, chemotactic and/or chemoattractant properties, and effects on cells including induction or inhibition of collagen synthesis, fibrosis, differentiation responses, cell proliferative responses and responses involving cell adhesion, migration and extracellular matrices. These properties make the proteins of the invention potential agents for wound healing, reduction of fibrosis and reduction of scar tissue formation.

Chordin, alone or complexed with monomrs, homodimers or heterodimers of BMPs, with members of the TGF-β superfamily of proteins, or with inhibin-α proteins or inhibin-β proteins, the chordin heterodimer is expected to demonstrate effects on the production of follicle stimulating hormone (FSH), as described further herein. It is recognized that FSH stimulates the development of ova in mammalian ovaries (Ross et al., in Textbook of Endocrinology, ed. Williams, p. 355 (1981) and that excessive stimulation of the ovaries with FSH will lead to multiple ovulations. FSH is also important in testicular function. Thus, chordin may be useful as a contraceptive based on the ability of inhibins to decrease fertility in female mammals and decrease spermatogenesis in male mammals. Administration of sufficient amounts of other inhibins can induce infertility in mammals. Chordin may also be useful as a fertility inducing therapeutic, based upon the ability of activin molecules in stimulating FSH release from cells of the anterior pituitary. See, for example, U.S. Pat. No. 4,798,885. Chordin may also be useful for advancement of the onset of fertility in sexually immature mammals, so as to increase the lifetime reproductive performance of domestic animals such as cows, sheep and pigs. It is further contemplated that chordin may be useful in modulating hematopoiesis by inducing the differentiation of erythroid cells [see, e.g., Broxmeyer et al, *Proc. Natl. Acad. Sci. USA,* 85: 9052–9056 (1988) or Eto et al, *Biochem. Biophys. Res. Comm.,* 142: 1095–1103 (1987)], for suppressing the development of gonadal tumors [see, e.g., Matzuk et al., *Nature,* 360: 313–319 (1992)] or for augmenting the activity of bone morphogenetic proteins [see, e.g., Ogawa et al., *J. Biol. Chem.,* 267: 14233–14237 (1992)].

Chordin proteins may be further characterized by their ability to modulate the release of follicle stimulating hormone (FSH) in established in vitro bioassays using rat anterior pituitary cells as described [see, e.g., Vale et al, *Endocrinology,* 91: 562–572 (1972); Ling et al., *Nature,* 321: 779–782 (1986) or Vale et al., *Nature,* 321: 776–779 (1986)]. It is contemplated that the chordin protein of the invention may bind to TGF-β proteins, which will have different effects depending upon whether they are in homodimeric or heterodimeric form. TGF-β proteins when found as a heterodimer with inhibin α or inhibin β chains, will exhibit regulatory effects, either stimulatory or inhibitory, on the release of follicle stimulating hormone (FSH), from anterior pituitary cells as described [Ling et al., *Nature,* 321: 779–782 (1986) or Vale et al., *Nature,* 321: 776–779 (1986); Vale et al, *Endocrinology,* 91: 562–572 (1972). Therefore, depending on the particular composition, it is expected that the chordin protein of the invention may have contrasting and opposite effects on the release of follicle stimulating hormone (FSH) from the anterior pituitary.

Activin A (the homodimeric composition of inhibin $β_A$) has been shown to have erythropoietic-stimulating activity [see e.g. Eto et al., *Biochem. Biophys. Res. Commun.,* 142: 1095–1103 (1987) and Murata et al., *Proc. Natl. Acad. Sci. U.S.A.,* 85: 2434–2438 (1988) and Yu et al., *Nature,* 330: 765–767 (1987)]. It is contemplated that the chordin protein of the invention may have a similar erythropoietic-stimulating activity. This activity of the chordin protein may be further characterized by the ability of the chordin protein to demonstrate erythropoietin activity in the biological assay performed using the human K-562 cell line as described by [Lozzio et al., *Blood,* 45: 321–334 (1975) and U.S. Pat. No. 5,071,834].

A further aspect of the invention is a therapeutic method and composition for repairing fractures and other conditions related to cartilage and/or bone and/or other connective tissue defects or periodontal diseases. The invention further comprises therapeutic methods and compositions for wound healing and tissue repair. Such compositions comprise a therapeutically effective amount of at least one of the chordin-related proteins of the invention in a mixture with a pharmaceutically acceptable vehicle, carrier or matrix. It is further contemplated that compositions of the invention may increase neuronal survival and therefore be useful in transplantation and treatment of conditions exhibiting a decrease in neuronal survival. Compositions of the invention may further include at least one other therapeutically useful agent, such as members of the TGF-β superfamily of proteins, which includes the BMP proteins BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; BMP-9, disclosed in PCT publication WO93/00432; BMP-10, disclosed in PCT application WO94/26893; BMP-11, disclosed in PCT application WO94/26892, BMP-12 or BMP-13, disclosed in PCT application WO 95/16035, or BMP-15, disclosed in co-pending patent application, Ser. No. 08/446,924, filed on May 18, 1995; or BMP-16, disclosed in co-pending patent application, Ser. No. 715,202, filed on Sep. 18, 1996. Other compositions which may also be useful include Vgr-2, and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of the above applications are hereby incorporated by reference herein.

It is expected that human chordin protein may exist in nature as homodimers or heterodimers. To promote the formation of dimers of chordin and useful proteins with increased stability, one can genetically engineer the DNA sequence of SEQUENCE ID NO: 1 to provide one or more additional cysteine residues to increase potential dimer formation. The resulting DNA sequence would be capable of producing a "cysteine added variant" of chordin. In a preferred embodiment, one would engineer the DNA sequence of SEQUENCE ID NO: 1 or SEQ ID NO: 2 so that one or more codons may be altered to a nucleotide triplet encoding a cysteine residue, such as TGT or TGC. Alternatively, one can produce "cysteine added variants" of chordin protein by altering the sequence of the protein at the amino acid level by altering one or more amino acid residues of SEQUENCE ID NO: 3 to Cys. Production of "cysteine added variants" of proteins is described in U.S. Pat. No. 5,166,322, the disclosure of which is hereby incorporated by reference.

It is expected that the proteins of the invention may act in concert with or perhaps synergistically with other related proteins and growth factors. Further therapeutic methods and compositions of the invention therefore comprise a therapeutic amount of at least one chordin protein of the invention with a therapeutic amount of at least one protein growth and/or differentiation factor, such as a member of the TGF-β superfamily of proteins, such as the BMP proteins disclosed in the applications described above. Such combinations may comprise chordin with separate molecules of the BMP proteins or heteromolecules comprised of different BMP moieties. For example, a method and composition of the invention may comprise a disulfide linked dimer comprising a chordin protein subunit and a subunit from one of the "BMP" proteins described above. Thus, the present invention includes a purified chordin-related polypeptide which is a heterodimer wherein one subunit comprises the amino acid sequence from amino acid #1 to amino acid #954 of SEQ ID NO: 3, and one subunit comprises an amino acid sequence for a bone morphogenetic protein selected from the group consisting of BMP-1, BMP-2, BMP-3, BMP-4, BMP-5, BMP-6, BMP-7, BMP-8, BMP-9, BMP-10, BMP-11, BMP-12 or BMP-13, disclosed in PCT application WO 95/16035, VGR-2, MP-52, BIP, the GDFs, HP-269, or BMP-15, disclosed in co-pending patent application, Ser. No. 08/446,924, filed on May 18, 1995; or BMP-16, disclosed in co-pending patent application, Ser. No. 715,202, filed on Sep. 18, 1996. A further embodiment may comprise a heterodimer of chordin-related moieties, for example of human chordin described herein and the *xenopus chordin* protein, which is the homologue of human chordin. Further, chordin protein may be combined with other agents beneficial to the treatment of the bone and/or cartilage and/or other connective tissue defect, wound, or tissue in question. These agents include various growth factors such as epidermal growth factor (EGF), fibroblast growth factor (FGF), platelet derived growth factor (PDGF), transforming growth factors (TGF-α and TGF-β), activins, inhibins, and k-fibroblast growth factor (kFGF), parathyroid hormone (PTH), parathyroid hormone related peptide (PTHrP), leukemia inhibitory factor (LIB/HILA/DA), insulin-like growth factors (IGF-I and IGF-II). Portions of these agents may also be used in compositions of the present invention. The preparation and formulation of such physiologically acceptable protein compositions, having due regard to pH, isotonicity, stability and the like, is within the skill of the art. The therapeutic compositions are also presently valuable for veterinary applications due to the lack of species specificity in growth and differentiation factors such as chordin. Particularly domestic animals and thoroughbred horses in addition to humans are desired patients for such treatment with the chordin proteins of the present invention.

The therapeutic method includes administering the composition topically, systemically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or other connective tissue or other tissue damage. Topical administration may be suitable for wound healing and tissue repair. Therapeutically useful agents other than the chordin proteins which may also optionally be included in the composition as described above, may alternatively or additionally, be administered simultaneously or sequentially with a BMP composition in the methods of the invention.

Preferably for bone and/or cartilage and/or other connective tissue formation, the composition includes a matrix capable of delivering chordin-related or other BMP proteins to the site of bone and/or cartilage and/or other connective tissue damage, providing a structure for the developing bone and cartilage and other connective tissue and optimally capable of being resorbed into the body. The matrix may provide slow release of chordin protein and/or other bone inductive protein, as well as proper presentation and appropriate environment for cellular infiltration. Such matrices may be formed of materials presently in use for other implanted medical applications.

The choice of matrix material is based on biocompatibility, biodegradability, mechanical properties, cosmetic appearance and interface properties. The particular application of the chordin compositions will define the appropriate formulation. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the chordin protein, e.g. amount of bone or other tissue weight desired to be formed, the site of bone or tissue damage, the condition of the damaged bone tissue, the size of a wound, type of damaged tissue, the patient's age, sex, and diet, the severity of any infection, time of administration and other clinical factors. The dosage may vary with the type of matrix used in the reconstitution and the types of BMP proteins in the composition. Generally, systemic or injectable administration will be initiated at a dose which is minimally effective, and the dose will be increased over a preselected time course until a positive effect is observed. Subsequently, incremental increases in dosage will be made limiting such incremental increases to such levels that produce a corresponding increase in effect, while taking into account any adverse affects that may appear. The addition of other known growth factors, such as IGF I (insulin like growth factor I), to the final composition, may also effect the dosage.

Progress can be monitored by periodic assessment of bone or tissue growth and/or repair. The progress can be monitored, for example, x-rays, histomorphometric determinations and tetracycline labeling.

The following examples illustrate practice of the present invention in recovering and characterizing human chordin and other chordin-related proteins, obtaining the human proteins and expressing the proteins via recombinant techniques.

EXAMPLES

Example 1
Description of the Isolation of the Human Chordin cDNA by Hybridization The human chordin full-length cDNA was isolated from a dT-primed cDNA library constructed in the plasmid vector pED6-dpc2. pED6-dpc2 is a derivative of the pED vector which is described in Kaufman et al., *Nucleic Acids Research*, 19: 4485–4490 (1991). cDNA was made from human liver RNA purchased from Clonetech. The probe sequences used to isolate chordin were derived from genomic fragments isolated by the inventors. The sequence of the two probes were as follows: 5'-CCACGTCTCGTCCAAGGCATAGACCTT-3' (SEQ ID NO:4) which is antisense sequence to the CR1 repeat of human chordin and 5'-CCAGCTCCGGTCACCATCAAAATAGCA-3' (SEQ ID NO:5) which is antisense sequence to the CR3 domain of human chordin. The DNA probes were radioactively labelled with $^{32}$P and used to screen the human liver dT-primed cDNA library, under high stringency hybridization/washing conditions, to identify clones containing sequences of the human chordin gene.

Sixty thousand library transformants were plated at a density of approximately 3000 transformants per plate on 20 plates. Nitrocellulose replicas of the transformed colonies were hybridized to the $^{32}$P labelled DNA probes in standard hybridization buffer (6X SSC, 0.5% SDS, 5X Denhardt's, 10 mM EDTA pH8, 100 mg/ml Bakers Yeast ribonucleic acid) under high stringency conditions (65° C. for 2 hours). After 2 hours hybridization, the radioactively labelled DNA probe containing hybridization solution was removed and the filters were washed under high stringency conditions (2X SSC, 0.5% SDS 21° C. for 5 minutes; followed by 2X SSC, 0.1% SDS 21° C. for 15 minutes; followed by a 2nd 2X SSC, 0.1% SDS 21° C. for 15 minutes; followed by 2X SSC, 0.1% SDS 65° C. for 10 minutes). The filters were wrapped in Saran wrap and exposed to X-ray film for overnight to 3 days at –80° C., with the aid of an intensifying screen. The autoradiographs were developed and positively hybridizing transformants of various signal intensities were identified. These positive clones were picked; grown for 5 hours in selective medium and plated at low density (approximately 100 colonies per plate). Nitrocellulose replicas of the colonies were hybridized to the $^{32}$P labelled probes in standard hybridization buffer (6X SSC, 0.5% SDS, 5X Denhardt's, 10 mM EDTA pH8, 100 mg/ml Bakers Yeast ribonucleic acid) under high stringency conditions (65° C. for 2 hours). After 2 hours hybridization, the radioactively labelled DNA probe containing hybridization solution was removed and the filters were washed under high stringency conditions (2X SSC, 0.5% SDS 21° C. for 5 minutes; followed by 2X SSC, 0.1% SDS 21° C. for 15 minutes; followed by a 2nd 2X SSC, 0.1% SDS 21° C. for 15 minutes; followed by 2X SSC, 0.1% SDS 65° C. for 10 minutes). The filters were wrapped in Saran wrap and exposed to X-ray film for overnight to 3 days at –80° C., with the aid of an intensifying screen. The autoradiographs were developed and positively hybridizing transformants were identified. Bacterial stocks of purified hybridization positive clones were made and plasmid DNA was isolated. The sequence of the cDNA insert was determined. The cDNA insert contained the sequences of both DNA probes used in the hybridization and contained the sequences for all 4 genomic fragments isolated by the inventors lab was pertained the 4 CRR domains of human chordin.

The chordin cDNA clone of SEQ ID NO: 1 was found to contain an incorrectly spliced intron that includes nucleotides #426 through #480 of the deposited cDNA clone; and contains a piece of the *H. sapiens* mitochondrial genome (Accession #V00662) from nucleotide #3517 through #4406 of the deposited cDNA clone. In order to overcome these problems, the inventors designed a synthetic sequence, shown in SEQ ID NO: 2, which can be used to express human chodin protein for use in the present invention.

Example 2
W-20 Bioassays

A. Description of W-20 Cells

Use of the W-20 bone marrow stromal cells as an indicator cell line is based upon the conversion of these cells to osteoblast-like cells after treatment with a BMP protein [Thies et al, *Journal of Bone and Mineral Research*, 5: 305 (1990); and Thies et al, *Endocrinology*, 130: 1318 (1992)]. Specifically, W-20 cells are a clonal bone marrow stromal cell line derived from adult mice by researchers in the laboratory of Dr. D. Nathan, Children's Hospital, Boston, Mass. Treatment of W-20 cells with certain BMP proteins results in (1) increased alkaline phosphatase production, (2) induction of PTH stimulated cAMP, and (3) induction of osteocalcin synthesis by the cells. While (1) and (2) represent characteristics associated with the osteoblast phenotype, the ability to synthesize osteocalcin is a phenotypic property only displayed by mature osteoblasts. Furthermore, to date we have observed conversion of W-20 stromal cells to osteoblast-like cells only upon treatment with BMPs. In this manner, the in vitro activities displayed by BMP treated W-20 cells correlate with the in vivo bone forming activity known for BMPs.

Below two in vitro assays useful in comparison of BMP activities of novel osteoinductive molecules are described.

B. W-20 Alkaline Phosphatase Assay Protocol

W-20 cells are plated into 96 well tissue culture plates at a density of 10,000 cells per well in 200 μl of media (DME with 10% heat inactivated fetal calf serum, 2 mM glutamine and 100 Units/ml penicillin+100 μg/ml streptomycin. The cells are allowed to attach overnight in a 95% air, 5% $CO_2$ incubator at 37° C. The 200 μl of media is removed from each well with a multichannel pipettor and replaced with an equal volume of test sample delivered in DME with 10% heat inactivated fetal calf serum, 2 mM glutamine and 1% penicillin-streptomycin. Test substances are assayed in triplicate. The test samples and standards are allowed a 24 hour incubation period with the W-20 indicator cells. After the 24 hours, plates are removed from the 37° C. incubator and the test media are removed from the cells. The W-20 cell layers are washed 3 times with 200 μl per well of calcium/magnesium free phosphate buffered saline and these washes are discarded. 50 μl of glass distilled water is added to each well and the assay plates are then placed on a dry ice/ethanol bath for quick freezing. Once frozen, the assay plates are removed from the dry ice/ethanol bath and thawed at 37° C. This step is repeated 2 more times for a total of 3 freeze-thaw procedures. Once complete, the membrane bound alkaline phosphatase is available for measurement. 50 μl of assay mix (50 mM glycine, 0.05% Triton X-100, 4 mM $MgCl_2$, 5 mM p-nitrophenol phosphate, pH=10.3) is added to each assay well and the assay plates are then incubated for 30 minutes at 37° C. in a shaking waterbath at 60 oscillations per minute. At the end of the 30 minute incubation, the reaction is stopped by adding 100 μl of 0.2N NaOH to each well and placing the assay plates on ice. The spectrophotometric absorbance for each well is read at a wavelength of 405 nanometers. These values are then compared to known standards to give an estimate of the alkaline phosphatase activity in each sample. For example, using known amounts of p-nitrophenol phosphate, absorbance values are generated. This is shown in Table I.

TABLE I

Absorbance Values for Known Standards of P-Nitrophenol Phosphate

| P-nitrophenol phosphate umoles | Mean absorbance (405 nm) |
|---|---|
| 0.000 | 0 |
| 0.006 | 0.261 +/− .024 |
| 0.012 | 0.521 +/− .031 |
| 0.018 | 0.797 +/− .063 |
| 0.024 | 1.074 +/− .061 |
| 0.030 | 1.305 +/− .083 |

Absorbance values for known amounts of BMPs can be determined and converted to μmoles of p-nitrophenol phosphate cleaved per unit time as shown in Table II.

TABLE II

Alkaline Phosphatase Values for W-20 Cells Treating with BMP-2

| BMP-2 concentration ng/ml | Absorbance Reading 405 nmeters | umoles substrate per hour |
|---|---|---|
| 0 | 0.645 | 0.024 |
| 1.56 | 0.696 | 0.026 |
| 3.12 | 0.765 | 0.029 |
| 6.25 | 0.923 | 0.036 |
| 12.50 | 1.121 | 0.044 |
| 25.0 | 1.457 | 0.058 |
| 50.0 | 1.662 | 0.067 |
| 100.0 | 1.977 | 0.080 |

These values are then used to compare the activities of known amounts of BMP-16 to BMP-2.

C. Osteocalcin RIA Protocol

W-20 cells are plated at $10^6$ cells per well in 24 well multiwell tissue culture dishes in 2 mls of DME containing 10% heat inactivated fetal calf serum, 2 mM glutamine. The cells are allowed to attach overnight in an atmosphere of 95% air 5% $CO_2$ at 37° C. The next day the medium is changed to DME containing 10% fetal calf serum, 2 mM glutamine and the test substance in a total volume of 2 ml. Each test substance is administered to triplicate wells. The test substances are incubated with the W-20 cells for a total of 96 hours with replacement at 48 hours by the same test medias. At the end of 96 hours, 50 μl of the test media is removed from each well and assayed for osteocalcin production using a radioimmunoassay for mouse osteocalcin. The details of the assay are described in the kit manufactured by Biomedical Technologies Inc., 378 Page Street, Stoughton, Mass. 02072. Reagents for the assay are found as product numbers BT-431 (mouse osteocalcin standard), BT-432 (Goat anti-mouse Osteocalcin), BT-431R (iodinated mouse osteocalcin), BT-415 (normal goat serum) and BT-414 (donkey anti goat IgG). The RIA for osteocalcin synthesized by W-20 cells in response to BMP treatment is carried out as described in the protocol provided by the manufacturer.

The values obtained for the test samples are compared to values for known standards of mouse osteocalcin and to the amount of osteocalcin produced by W-20 cells in response to challenge with known amounts of BMP-2. The values for BMP-2 induced osteocalcin synthesis by W-20 cells is shown in Table III.

TABLE III

Osteocalcin Synthesis by W-20 Cells

| BMP-2 Concentration ng/ml | Osteocalcin Synthesis ng/well |
|---|---|
| 0 | 0.8 |
| 2 | 0.9 |
| 4 | 0.8 |
| 8 | 2.2 |
| 16 | 2.7 |
| 31 | 3.2 |
| 62 | 5.1 |
| 125 | 6.5 |
| 250 | 8.2 |
| 500 | 9.4 |
| 1000 | 10.0 |

Example 3
Rosen Modified Sampath-Reddi Assay

A modified version of the rat bone formation assay described in Sampath and Reddi, *Proc. Natl. Acad. Sci. USA*, 80: 6591–6595 (1983) is used to evaluate bone and/or cartilage and/or other connective tissue activity of BMP proteins. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then equilibrated to 0.1% TFA. The resulting solution is added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans Rats. The implants are removed after 7–14 days. Half of each implant is used for alkaline phosphatase analysis [see, Reddi et al, *Proc. Natl. Acad. Sci.*, 69: 1601 (1972)].

The other half of each implant is fixed and processed for histological analysis. 1 μm glycolmethacrylate sections are stained with Von Kossa and acid fuschin to score the amount of induced bone and cartilage and other connective tissue formation present in each implant. The terms +1 through +5 represent the area of each histological section of an implant occupied by new bone and/or cartilage cells and matrix. A score of +5 indicates that greater than 50% of the implant is new bone and/or cartilage produced as a direct result of protein in the implant. A score of +4, +3, +2, and +1 would indicate that greater than 40%, 30%, 20% and 10% respectively of the implant contains new cartilage and/or bone.

Alternatively, the implants are inspected for the appearance of tissue resembling embryonic tendon, which is easily recognized by the presence of dense bundles of fibroblasts oriented in the same plane and packed tightly together. [Tendon/ligament-like tissue is described, for example, in Ham and Cormack, *Histology* (JB Lippincott Co. (1979), pp. 367–369, the disclosure of which is hereby incorporated by reference]. These findings may be reproduced in additional assays in which tendon/ligament-like tissues are observed in the chordin-related protein containing implants. The chordin-related proteins of this invention may be assessed for activity on this assay.

Example 4
Expression of Chordin

In order to produce murine, human or other mammalian chordin-related proteins, the DNA encoding it is transferred into an appropriate expression vector and introduced into mammalian cells or other preferred eukaryotic or prokaryotic hosts by conventional genetic engineering techniques. The preferred expression system for biologically active recombinant human chordin is contemplated to be stably transformed mammalian cells.

One skilled in the art can construct mammalian expression vectors by employing the sequence of SEQ ID NO: 1 or SEQ ID NO: 3, or other DNA sequences encoding chordin-related proteins or other modified sequences and known vectors, such as pCD [Okayama et al., Mol. Cell Biol., 2: 161–170 (1982)], pJL3, pJL4 [Gough et al., EMBO J., 4: 645–653 (1985)] and pMT2 CXM.

The mammalian expression vector pMT2 CXM is a derivative of p91023(b) (Wong et al., Science 228: 810–815, 1985) differing from the latter in that it contains the ampicillin resistance gene in place of the tetracycline resistance gene and further contains a XhoI site for insertion of cDNA clones. The functional elements of pMT2 CXM have been described (Kaufman, R. J., 1985, Proc. Natl. Acad. Sci. USA 82: 689–693) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in E. coli.

Plasmid pMT2 CXM is obtained by EcoRI digestion of pMT2-VWF, which has been deposited with the American Type Culture Collection (ATCC), Rockville, Md. (USA) under accession number ATCC 67122. EcoRI digestion excises the cDNA insert present in pMT2-VWF, yielding pMT2 in linear form which can be ligated and used to transform E. coli HB 101 or DH-5 to ampicillin resistance. Plasmid pMT2 DNA can be prepared by conventional methods. pMT2 CXM is then constructed using loopout/in mutagenesis [Morinaga, et al., Biotechnology 84: 636 (1984). This removes bases 1075 to 1145 relative to the Hind III site near the SV40 origin of replication and enhancer sequences of pMT2. In addition it inserts the following sequence:

5' PO-CATGGGCAGCTCGAG-3' (SEQ ID NO:6)

at nucleotide 1145. This sequence contains the recognition site for the restriction endonuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

pEMC2β1 derived from pMT21 may also be suitable in practice of the invention. pMT21 is derived from pMT2 which is derived from pMT2-VWF. As described above EcoRI digestion excises the cDNA insert present in pMT-VWF, yielding pMT2 in linear form which can be ligated and used to transform E. coli HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a XhoI site is inserted to obtain the following sequence immediately upstream from DHFR: 5'-

CTGCAGGCGAGCCTGAATTCCTCGAGCCATCATG-3' (SEQ ID NO:7)

Second, a unique ClaI site is introduced by digestion with EcoRV and XbaI, treatment with Klenow fragment of DNA polymerase I, and ligation to a ClaI linker (CATCGATG). This deletes a 250 bp segment from the adenovirus associated RNA (VAI) region but does not interfere with VAI RNA gene expression or function. pMT21 is digested with EcoRI and XhoI, and used to derive the vector pEMC2B1.

A portion of the EMCV leader is obtained from pMT2-ECAT1 [S. K. Jung, et al, J. Virol 63: 1651–1660 (1989)] by digestion with Eco RI and PstI, resulting in a 2752 bp fragment. This fragment is digested with TaqI yielding an Eco RI-TaqI fragment of 508 bp which is purified by electrophoresis on low melting agarose gel. A 68 bp adapter and its complementary strand are synthesized with a 5' TaqI protruding end and a 3' XhoI protruding end which has the following sequence:

5'CGAGGTTAAAAAACGTCTAGGCCCCCCGAACCACGGGGACGTGGTTTTCCTTT

GAAAAACACGATTGC-3' (SEQ ID NO:8)
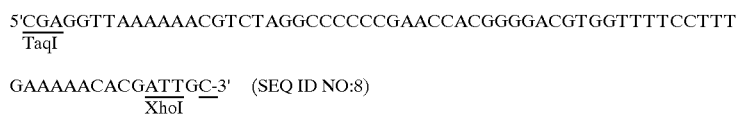

This sequence matches the EMC virus leader sequence from nucleotide 763 to 827. It also changes the ATG at position 10 within the EMC virus leader to an ATT and is followed by a XhoI site. A three way ligation of the pMT21 Eco RI-16hoI fragment, the EMC virus EcoRI-TaqI fragment, and the 68 bp oligonucleotide adapter TaqI-16hoI adapter resulting in the vector pEMC2β1.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells.

The construction of vectors may involve modification of the chordin-related DNA sequences. For instance, chordin cDNA can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of chordin-related proteins. Additionally, the sequence of SEQ ID NO: 1 or SEQ ID NO: 3 or other sequences encoding chordin-related proteins can be manipulated to express a mature chordin-related protein by deleting chordin encoding propeptide sequences and replacing them with sequences encoding the complete propeptides of other BMP proteins.

One skilled in the art can manipulate the sequences of SEQ ID NO: 1 by eliminating or replacing the mammalian regulatory sequences flanking the coding sequence with bacterial sequences to create bacterial vectors for intracellular or extracellular expression by bacterial cells or other prokaryotic hosts. For example, the coding sequences could be further manipulated (e.g. ligated to other known linkers or modified by deleting non-coding sequences therefrom or altering nucleotides therein by other known techniques). The modified chordin-related coding sequence could then be inserted into a known bacterial vector using procedures such as described in T. Taniguchi et al., *Proc. Natl Acad. Sci. USA*, 77: 5230–5233 (1980). This exemplary bacterial vector could then be transformed into bacterial host cells and a chordin-related protein expressed thereby. For a strategy for producing extracellular expression of chordin-related proteins in bacterial cells, see, e.g. European patent application EPA 177,343. Alternatively, high level expression of chordin-related protein in bacterial cells, particularly, *E. coli* cells, may be achieved by fusion of the chordin coding sequence to the 3' end of the gene for the native *E. coli* protein thioredoxin. LaVallie et al., *Bio/Technology*, 11: 187–192 (1993).

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a chordin-related protein of the invention in mammalian cells may involve the construction of cells containing multiple copies of the heterologous chordin-related gene. The heterologous gene is linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.*, 159: 601–629 (1982). This approach can be employed with a number of different cell types.

For example, a plasmid containing a DNA sequence for a chordin-related protein of the invention in operative association with other plasmid sequences enabling expression thereof and the DHFR expression plasmid pAdA26SV(A)3 [Kaufman and Sharp, *Mol. Cell. Biol.*, 2: 1304 (1982)] can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (e.g. sequential steps in 0.02, 0.2, 1.0 and 5 uM MTX) as described in Kaufman et al., *Mol Cell Biol.*, 5: 1750 (1983). Transformants are cloned, and biologically active chordin expression is monitored by the Rosen-modified Sampath-Reddi rat bone formation assay described above in Example 3, or by BMP binding as shown in Example 8. Chordin protein expression should increase with increasing levels of MTX resistance. Chordin polypeptides are characterized using standard techniques known in the art such as pulse labeling with [35S] methionine or cysteine and polyacrylamide gel electrophoresis. Similar procedures can be followed to produce other chordin-related proteins.

Example 5
Biological Activity of Expressed Chordin

To measure the biological activity of the expressed chordin-related proteins obtained in Example 4 above, the proteins are recovered from the cell culture and purified by isolating the chordin-related proteins from other proteinaceous materials with which they are co-produced as well as from other contaminants. The purified protein may be assayed in accordance with the rat bone formation assay described in Example 3.

Purification is carried out using standard techniques known to those skilled in the art.

Protein analysis is conducted using standard techniques such as SDS-PAGE acrylamide [Laemmli, *Nature* 227: 680 (1970)] stained with silver [Oakley, et al. *Anal. Biochem.* 105: 361 (1980)] and by immunoblot [Towbin, et al. *Proc. Natl. Acad. Sci. USA* 76: 4350 (1979)]

Example 6
Northern Analyses

Using Northern analysis, chordin and chordin-related proteins can be tested for their effects on various cell lines. Suitable cell lines include cell lines derived from E13 mouse limb buds. After 10 days of treatment with chordin or chordin-related protein, the cell phenotype is examined histologically for indications of tissue differentiation. In addition, Northern analysis of mRNA from chordin or chordin-related protein treated cells can be performed for various markers including one or more of the following markers for bone, cartilage and/or tendon/ligament, as described in Table IV:

TABLE IV

| Marker | Bone | Cartilage | Tendon/Ligament |
|---|---|---|---|
| Osteocalcin | + | − | − |
| Alkaline Phosphatase | + | − | − |
| Proteoglycan Core Protein | +/−[1] | + | +[2] |
| Collagen Type I | + | + | + |
| Collagen Type II | +/−[1] | + | +[2] |
| Decorin | + | + | + |
| Elastin | +/−[3] | ? | + |

[1]Marker seen early, marker not seen as mature bone tissue forms
[2]Marker depends upon site of tendon; strongest at bone interface
[3]Marker seen at low levels Example 7
Embryonic Stem Cell Assay In order to assay the effects of the chordin proteins of the present invention, it is possible to assay the growth and differentiation effects in vitro on a number of available embryonic stem cell lines. One such cell line is ES-E14TG2, which is available from the American Type Culture Collection in Rockville, Md.

In order to conduct the assay, cells may be propagated in the presence of 100 units of LIF to keep them in an undifferentiated state. Assays are setup by first removing the LIF and aggregating the cells in suspension, in what is known as embryoid bodies. After 3 days the embryoid bodies are plated on gelatin coated plates (12 well plates for PCR analysis, 24 well plates for immunocytochemistry) and treated with the proteins to be assayed. Cells are supplied with nutrients and treated with the protein factor every 2–3 days. Cells may be adapted so that assays may be conducted in media supplemented with 15% Fetal Bovine Serum (FBS) or with CDM defined media containing much lower amounts of FBS.

At the end of the treatment period (ranging from 7–21 days) RNA is harvested from the cells and analyzed by quantitative multiplex PCR for the following markers: Brachyury, a mesodermal marker, AP-2, an ectodermal marker, and HNF-3α an endodermal marker. Through immunocytochemistry, it is also possible to detect the differentiation of neuronal cells (glia and neurons), muscle cells (cardiomyocytes, skeletal and smooth muscle), and various other phenotype markers such as proteoglycan core protein (cartilage), and cytokeratins (epidermis). Since these cells have a tendency to differentiate autonomously when LIF is removed, the results are always quantitated by comparison to an untreated control.

Example 8

BMP Binding

The chordin and chordin-related polypeptides of the present invention may be assayed for binding to BMPs, other TGF-β proteins, or other ligands in any manner known in the art, including the following methods:

Ligand Blotting: The binding protein [chordin or chordin-related polypeptide] is run on SDS-PAGE, transferred to a membrane (such as a Western blot) and probed with iodinated ligand. Fukui et al., *Developmental Biology*, 159: 131–139 (1993).

Gel Filtration: The binding protein [chordin or chordin-related polypeptide] is incubated with iodinated ligand and and ligand-binding protein complex is separated from unbound species by size using gel filtration. Vaughn and Vale, *Endocrinology*, 132: 2038–2050 (1993).

Cross-Linking: The binding protein [chordin or chordin-related polypeptide] is incubated with iodinated ligand and covalently coupled with chemical cross-linker. The reaction mix is run on SDS-PAGE. Autoradiography will reveal complex formation via binding of ligand to binding protein. Vaughn and Vale, *Endocrinology*, 132: 2038–2050 (1993).

Immunoprecipitation: The binding protein [chordin or chordin-related polypeptide] is incubated with iodinated ligand and covalently coupled with chemical cross-linker. The reaction mix is then immunoprecipitated with ligand antibody. The immunoprecipitate is run on SDS-PAGE. Vaughn and Vale, *Endocrinology*, 132: 2038–2050 (1993).

Gel Shift: The binding protein [chordin or chordin-related polypeptide] is incubated with iodinated ligand and run on non-denaturing agarose gel. The complex is identified by autoradiography. Krumment at al., *Endocrinology*, 132: 431–443 (1993).

Radioreceptor Binding Assay: The ligand is iodinated and specific activity is determined. The cell surface receptor binding assay described in Massague, *Methods in Enzymology*, 46: 174–195 (1987) is performed using 10T1/2 cells, or other suitable cell line. The cells are allowed to reach confluency in suitable medium, rinsed, and incubated with iodinated ligand containing increasing concentrations of binding protein [chordin or chordin-related polypeptide] at room temperature for one hour. The plates are chilled and rinsed. The bound iodinated ligand is solubilized with solubilization buffer and counted with a gamma counter. Massague, Id.

The above references are hereby incorporated herein by reference for their full disclosure of the methods and materials useful in the above procedures.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

ATCC Deposits

The following materials have been deposited with the American Type Culture Collection (ATCC), Rockville, Md. (USA) under the Budapest Treaty. pCHD__1A/DH10B, a plasmid containing the DNA sequence of human chordin [SEQ ID NO: 1] was deposited on Nov. 12, 1996. ATCC accession number ATCC 68258.

---

What is claimed is:

1. An isolated DNA molecule comprising a DNA sequence selected from the group consisting of:
   (a) nucleotides #1 to #4425 of SEQ ID NO: 1;
   (b) nucleotide #1, 64, 70 or 79 to #2862 of SEQ ID NO: 2;
   (c) nucleotides encoding amino acids #1, 22, 24 or 27 to #954 of SEQ ID NO: 3;
   (d) naturally occurring human allelic sequences of (a), (b) or (c); and
   (e) degenerative codon sequences (a), (b), (c) or (d).

2. A host cell transformed with the DNA sequence of claim 1.

3. A vector comprising a DNA molecule of claim 1 in operative association with an expression control sequence therefor.

4. A host cell transformed with the vector of claim 3.

5. An isolated DNA molecule comprising a DNA sequence consisting of nucleotides #70 to #2862 of SEQ ID NO: 2.

6. A vector comprising a DNA molecule of claim 5 in operative association with an expression control sequence therefor.

7. A host cell transformed with the vector of claim 6.

8. A host cell according to claim 7, further transformed with a vector comprising a DNA molecule encoding a bone morphogenetic protein.

9. A method for producing a purified human chordin protein, said method comprising the steps of:
   (a) culturing a host cell transformed with a DNA molecule according to claim 1; and
   (b) recovering and purifying said human chordin protein from the culture medium.

10. The method of claim 9, wherein said host cell is transformed with a DNA molecule comprising a DNA coding sequence consisting of nucleotide #70 to #2862 of SEQ ID NO: 2.

11. The method of claim 10, wherein said host cell is a mammalian cell and the DNA molecule further comprises a DNA sequence encoding a propeptide from a member of the TGF-β superfamily of proteins, said DNA sequence encoding a propeptide being linked in proper reading frame to the DNA coding sequence.

12. A chimeric DNA molecule comprising a DNA sequence encoding a propeptide from a member of the TGF-β superfamily of proteins linked in frame to a DNA sequence encoding a chordin polypeptide, said chordin polypeptide comprising amino acid #1 to #954 of SEQ ID NO: 3.

* * * * *